(12) United States Patent  
Adams et al.

(10) Patent No.: US 8,434,161 B1  
(45) Date of Patent: Apr. 30, 2013

(54) CANTILEVERED PROBE DETECTOR WITH PIEZOELECTRIC ELEMENT

(75) Inventors: Jesse D. Adams, Reno, NV (US); Todd A. Sulchek, Oakland, CA (US); Stuart C. Feigin, Reno, NV (US)

(73) Assignee: Board of Regents of the Nevada System of Higher Education, on behalf of the University of Nevada, Reno, NV (US)

( * ) Notice: Subject to any disclaimer, the term of this patent is extended or adjusted under 35 U.S.C. 154(b) by 0 days.

(21) Appl. No.: 13/539,608

(22) Filed: Jul. 2, 2012

Related U.S. Application Data

(63) Continuation of application No. 11/845,661, filed on Aug. 27, 2007, now Pat. No. 8,136,385, which is a continuation of application No. 11/576,443, filed as application No. PCT/US2005/035216 on Sep. 30, 2005, now Pat. No. 7,694,346.

(60) Provisional application No. 60/614,592, filed on Oct. 1, 2004.

(51) Int. Cl.  
*G01Q 70/08* (2010.01)

(52) U.S. Cl.  
USPC ............... 850/56; 250/234; 250/288; 422/50; 422/82.01; 422/68.01; 436/183; 436/164; 850/7; 850/57; 850/9; 850/10; 850/59

(58) Field of Classification Search .................. 250/234, 250/288; 422/50, 82.01, 68.01; 436/183, 436/164; 850/7, 57, 56, 9, 10, 59  
See application file for complete search history.

(56) References Cited

U.S. PATENT DOCUMENTS 3,164,004 A    1/1965   King  
3,266,291 A    8/1966   King  
(Continued)

FOREIGN PATENT DOCUMENTS

EP      0282251 A2    9/1988  
GB      2432001       4/2009  
(Continued)

OTHER PUBLICATIONS

Official Action issued in U.S. Appl. No. 13/350,921, dated Jun. 26, 2012, 16 pages.

(Continued)

*Primary Examiner* — Jack Berman  
*Assistant Examiner* — Meenakshi Sahu  
(74) *Attorney, Agent, or Firm* — Wood, Herron & Evans, LLP

(57) ABSTRACT

A disclosed chemical detection system for detecting a target material, such as an explosive material, can include a cantilevered probe, a probe heater coupled to the cantilevered probe, and a piezoelectric element disposed on the cantilevered probe. The piezoelectric element can be configured as a detector and/or an actuator. Detection can include, for example, detecting a movement of the cantilevered probe or a property of the cantilevered probe. The movement or a change in the property of the cantilevered probe can occur, for example, by adsorption of the target material, desorption of the target material, reaction of the target material and/or phase change of the target material. Examples of detectable movements and properties include temperature shifts, impedance shifts, and resonant frequency shifts of the cantilevered probe. The overall chemical detection system can be incorporated, for example, into a handheld explosive material detection system.

30 Claims, 11 Drawing Sheets

U.S. PATENT DOCUMENTS

| | | |
|---|---|---|
| 3,478,573 A | 11/1969 | King |
| 3,715,911 A | 2/1973 | Chuan |
| 4,312,288 A | 1/1982 | Finsterwalder et al. |
| 4,549,427 A | 10/1985 | Kolesar, Jr. |
| 4,637,987 A | 1/1987 | Minten et al. |
| 4,674,319 A | 6/1987 | Muller et al. |
| 4,747,698 A | 5/1988 | Wickramasinghe et al. |
| 4,935,634 A | 6/1990 | Hansma et al. |
| 4,992,244 A | 2/1991 | Grate |
| 5,187,367 A | 2/1993 | Miyazaki et al. |
| 5,266,801 A | 11/1993 | Elings et al. |
| 5,345,213 A | 9/1994 | Semancik et al. |
| 5,356,756 A | 10/1994 | Cavicchi et al. |
| 5,411,709 A | 5/1995 | Furuki et al. |
| 5,412,980 A | 5/1995 | Elings et al. |
| 5,445,008 A | 8/1995 | Wachter et al. |
| 5,469,369 A | 11/1995 | Rose-Pehrsson et al. |
| 5,519,212 A | 5/1996 | Elings et al. |
| 5,719,324 A * | 2/1998 | Thundat et al. ............ 73/24.01 |
| 5,742,377 A | 4/1998 | Minne et al. |
| 5,750,989 A | 5/1998 | Lindsay et al. |
| 5,753,814 A | 5/1998 | Han et al. |
| 5,756,631 A | 5/1998 | Grate |
| 5,807,758 A | 9/1998 | Lee et al. |
| 5,874,668 A | 2/1999 | Xu et al. |
| 5,883,705 A | 3/1999 | Minne et al. |
| 5,918,263 A * | 6/1999 | Thundat ............ 73/35.16 |
| 5,965,452 A | 10/1999 | Kovacs |
| 6,005,400 A | 12/1999 | Thundat et al. |
| 6,015,869 A | 1/2000 | Grate et al. |
| 6,016,686 A | 1/2000 | Thundat |
| 6,029,500 A | 2/2000 | Tom |
| 6,032,518 A | 3/2000 | Prater et al. |
| 6,041,642 A | 3/2000 | Duncan |
| 6,050,722 A | 4/2000 | Thundat et al. |
| 6,075,585 A | 6/2000 | Minne et al. |
| 6,096,559 A | 8/2000 | Thundat et al. |
| 6,118,124 A | 9/2000 | Thundat et al. |
| 6,156,578 A | 12/2000 | Tom |
| 6,167,748 B1 | 1/2001 | Britton, Jr. et al. |
| 6,182,499 B1 | 2/2001 | McFarland et al. |
| 6,185,992 B1 | 2/2001 | Daniels et al. |
| 6,189,374 B1 | 2/2001 | Adderton et al. |
| 6,212,939 B1 | 4/2001 | Thundat |
| 6,253,162 B1 | 6/2001 | Jarman et al. |
| 6,263,736 B1 | 7/2001 | Thundat et al. |
| 6,269,685 B1 | 8/2001 | Oden |
| 6,280,939 B1 | 8/2001 | Allen |
| 6,289,717 B1 | 9/2001 | Thundat et al. |
| 6,295,861 B1 | 10/2001 | Tom et al. |
| 6,311,549 B1 | 11/2001 | Thundat et al. |
| 6,311,557 B1 | 11/2001 | Davis et al. |
| 6,312,959 B1 | 11/2001 | Datskos |
| 6,336,353 B2 | 1/2002 | Matsiev et al. |
| 6,336,366 B1 | 1/2002 | Thundat et al. |
| 6,386,053 B1 | 5/2002 | Takeuchi et al. |
| 6,393,895 B1 | 5/2002 | Matsiev et al. |
| 6,401,519 B1 | 6/2002 | McFarland et al. |
| 6,408,250 B1 | 6/2002 | Grate et al. |
| 6,411,075 B1 | 6/2002 | Battiston et al. |
| 6,436,346 B1 | 8/2002 | Doktycz et al. |
| 6,437,328 B1 | 8/2002 | Knauss et al. |
| 6,455,319 B1 | 9/2002 | Lewis et al. |
| 6,457,360 B1 | 10/2002 | Daraktchiev et al. |
| 6,469,293 B1 | 10/2002 | Shimizu et al. |
| 6,477,479 B1 | 11/2002 | Mansky et al. |
| 6,487,523 B2 | 11/2002 | Jarman et al. |
| 6,494,079 B1 | 12/2002 | Matsiev et al. |
| 6,523,392 B2 | 2/2003 | Porter et al. |
| 6,530,266 B1 | 3/2003 | Adderton et al. |
| 6,535,822 B2 | 3/2003 | Mansky et al. |
| 6,535,824 B1 | 3/2003 | Mansky et al. |
| 6,545,495 B2 | 4/2003 | Warmack et al. |
| 6,575,020 B1 | 6/2003 | De Charmoy Grey et al. |
| 6,598,459 B1 | 7/2003 | Fu |
| 6,606,567 B2 | 8/2003 | Grate et al. |
| 6,650,102 B2 | 11/2003 | Hajduk et al. |
| 6,668,627 B2 | 12/2003 | Lange et al. |
| 6,672,144 B2 | 1/2004 | Adderton et al. |
| 6,763,705 B1 | 7/2004 | Thundat et al. |
| 6,797,631 B2 | 9/2004 | Kim et al. |
| 6,810,720 B2 | 11/2004 | Adderton et al. |
| 6,811,133 B2 | 11/2004 | Miles |
| 6,815,866 B2 | 11/2004 | Lee |
| 6,823,717 B2 | 11/2004 | Porter et al. |
| 6,854,317 B2 | 2/2005 | Porter et al. |
| 6,866,819 B1 | 3/2005 | Chandra et al. |
| 6,904,786 B2 | 6/2005 | Matsiev et al. |
| 6,928,877 B2 | 8/2005 | Carlson et al. |
| 6,935,165 B2 | 8/2005 | Bashir et al. |
| 6,953,977 B2 | 10/2005 | Mlcak et al. |
| 6,955,787 B1 | 10/2005 | Hanson |
| 6,957,565 B2 | 10/2005 | Matsiev et al. |
| 7,260,980 B2 | 8/2007 | Adams |
| 7,375,321 B2 | 5/2008 | Roukes et al. |
| 7,521,257 B2 | 4/2009 | Adams |
| 7,560,070 B1 | 7/2009 | Baller et al. |
| 7,694,346 B2 * | 4/2010 | Adams et al. ............ 850/7 |
| 8,220,067 B2 * | 7/2012 | Adams et al. ............ 850/56 |
| 2001/0000279 A1 | 4/2001 | Daniels et al. |
| 2001/0029774 A1 | 10/2001 | Grate et al. |
| 2002/0032531 A1 | 3/2002 | Mansky et al. |
| 2002/0062684 A1 | 5/2002 | Adderton et al. |
| 2002/0092359 A1 | 7/2002 | Lange et al. |
| 2002/0178787 A1 | 12/2002 | Matsiev et al. |
| 2003/0000291 A1 | 1/2003 | Kolosov et al. |
| 2003/0032293 A1 * | 2/2003 | Kim et al. ............ 438/694 |
| 2003/0041653 A1 | 3/2003 | Matsiev et al. |
| 2003/0041676 A1 | 3/2003 | Hajduk et al. |
| 2003/0045019 A1 | 3/2003 | Kubena |
| 2003/0089182 A1 | 5/2003 | Thaysen et al. |
| 2003/0101006 A1 | 5/2003 | Mansky et al. |
| 2003/0154771 A1 | 8/2003 | De Charmoy Grey et al. |
| 2003/0166039 A1 | 9/2003 | Hubler et al. |
| 2003/0218467 A1 | 11/2003 | Carlson et al. |
| 2004/0074303 A1 | 4/2004 | Matsiev et al. |
| 2004/0099050 A1 | 5/2004 | Matsiev et al. |
| 2004/0223884 A1 | 11/2004 | Chen et al. |
| 2004/0244487 A1 | 12/2004 | Kolosov et al. |
| 2004/0250622 A1 | 12/2004 | Kolosov et al. |
| 2004/0255651 A1 | 12/2004 | Adderton et al. |
| 2005/0009197 A1 | 1/2005 | Adams et al. |
| 2005/0016276 A1 | 1/2005 | Guan et al. |
| 2005/0034542 A1 | 2/2005 | Thaysen |
| 2005/0066714 A1 | 3/2005 | Adderton et al. |
| 2005/0133877 A1 | 6/2005 | Thaysen et al. |
| 2005/0164299 A1 | 7/2005 | Stewart |
| 2005/0166679 A1 | 8/2005 | Carlson et al. |
| 2005/0199047 A1 | 9/2005 | Adams |
| 2005/0229713 A1 | 10/2005 | Niblock |
| 2006/0032289 A1 | 2/2006 | Pinnaduwage et al. |
| 2006/0257286 A1 | 11/2006 | Adams |
| 2009/0229020 A1 | 9/2009 | Adams |
| 2011/0003718 A1 * | 1/2011 | Adams ............ 506/39 |
| 2012/0115757 A1 * | 5/2012 | Adams ............ 506/39 |
| 2012/0172256 A1 * | 7/2012 | Adams et al. ............ 506/12 |

FOREIGN PATENT DOCUMENTS

| | | |
|---|---|---|
| GB | 2437753 | 4/2009 |
| WO | WO00/20850 A1 | 4/2000 |
| WO | WO03/044530 A1 | 5/2003 |
| WO | WO03/062135 A1 | 7/2003 |
| WO | WO03/067248 A1 | 8/2003 |
| WO | WO03/071258 A1 | 8/2003 |
| WO | WO 03/095616 A2 | 11/2003 |
| WO | WO03/104784 A1 | 12/2003 |
| WO | WO2004/059306 A1 | 7/2004 |
| WO | WO2004/083802 A1 | 9/2004 |
| WO | WO 2005/029042 A2 | 3/2005 |
| WO | WO2005/083409 A1 | 9/2005 |
| WO | WO2006/039506 A3 | 4/2006 |

OTHER PUBLICATIONS

Notice of Allowance issued in U.S. Appl. No. 12/748,788, dated Mar. 20, 2012, 31 pages.

Notice of Allowance issued in U.S. Appl. No. 11/576,443, dated Jan. 28, 2010, 44 pages.

Adams, et al., "Taking Atomic Force Microscopy Advances to the University Classroom," *Aerospace Conference, 2001, IEEE Proceedings* Mar. 10, 2001-Mar. 17, 2001 7:7-3673-7-3682 (2001).
Adams, et al., Office Action Response Regarding U.S. Appl. No. 11/089,559 (Apr. 12, 2007).
Adams, et al., Office Action Response Regarding U.S. Appl. No. 11/089,559 (Nov. 10, 2006).
Adams, et al., Office Action Response Regarding U.S. Appl. No. 11/089,559 (Apr. 13, 2006).
Adams, et al., Response to Restriction Requirement Regarding U.S. Appl. No. 11/089,559 (Aug. 19, 2005).
Adams, Office Action Response Regarding U.S. Appl. No. 10/967,748 (Nov. 22, 2006).
Adams, Office Action Response Regarding U.S. Appl. No. 10/967,748 (Mar. 6, 2006).
Adams, Office Action Response Regarding U.S. Appl. No. 10/967,748 (Jul. 11, 2005).
Adams, et al., Response to Office Action Regarding U.S. Appl. No. 10/777,282 (Oct. 27, 2008).
Adams, et al., Response to Office Action Regarding U.S. Appl. No. 10/777,282 (Mar. 25, 2008).
Adams, U.S. Appl. No. 11/845,680, filed Aug. 27, 2007, not yet published.
Barrettino, et al., "CMOS Monolithic Mechatronic Microsystem for Surface Imaging and Force Response Studies," *IEEE Journal of Solid-State Circuits* 40(4):951-959 (Apr. 2005).
Binnig, et al., "Ultrahigh-density Atomic Force Microscopy Data Storage With Erase Capability," *Applied Physics Letters* 74(9):1329-1331 (Mar. 1, 1999).
Boakes, Response to Examination Report, GB Application 0609690.3 (Jul. 7, 2008).
Boakes, Response to Examination Report, GB Application 0609690.3 (Dec. 9, 2008).
Boakes, Response to Examination Report, GB Application 0609690.3 (Feb. 19 2009).
Boakes, Response to Examination Report, GB Application 0708212.6 (Feb. 6, 2009).
Bustillo, et al., "Surface Micromachining for Microelectromechanical Systems," *Proceedings of the IEEE* 86(8):1552-1574 (Aug. 1998).
Itoh, et al., "Piezoelectric Cantilever Array for Multiprobe Scanning Force Microscopy," *Micro Electro Mechanical Systems, 1996, MEMS '96, Proceedings. 'An Investigation of Micro Structures, Sensors, Actuators, Machines and Systems'. IEEE, The Ninth Annual International Workshop on* 451-455 (Feb. 11, 1996).
Jones, Examination Report, GB Application 0609690.3 (Jan 14, 2008).
Jones, Examination Report, GB Application 0609690.3 (Oct. 21, 2008).
Jones, Examination Report, GB Application 0609690.3 (Dec. 22, 2008).
Kim, et al., "Parallel Frequency Readout of an Array of Mass-Sensitive Transducers for Sensor Applications," *Microelectrical Engineering* 53:229-232 (2000).
Liu, et al., "On the Modes and Loss Mechanisms of a High Q Mechanical Oscillator," *Applied Physics Letters* 78(10):1346-1348 (Mar. 5, 2001).
Mathieu, et al., "Piezoresistive Signal Down Mixing for Parallel Detection of Si-based Microcantilevers Resonant Frequencies," *Sensors, 2005 IEEE* 708-711 (Oct. 30, 2005).
Minne, et al., "Parallel Atomic Force Microscopy Using Cantilevers With Integrated Piezoresistive Sensors and Integrated Piezoelectric Actuators," *Applied Physics Letters* 67(26):3918-3920 (Dec. 25, 1995).
Moss, Office Action Regarding U.S. Appl. No. 10/777,282 (Oct. 25, 2007).
Moss, Office Action Regarding U.S. Appl. No. 10/777,282 (Jul. 29, 2008).
Omote, et al., "Temperature Dependence of Elastic, Dielectric, and Piezoelectric Properties of 'Single Crystalline' Films of Vinylidene Fluoride Trifluoroethylene Copolymer," *Journal of Applied Physics* 81(6):2760-2769 (Mar. 15, 1997).

Phipps, Examination Report, GB Application 0708212.6 (Apr. 2, 2008).
Phipps, Examination Report, GB Application 07082 2.6 (Dec. 9, 2008).
Raevis, Interview Summary Regarding U.S. Appl. No. 11/089,559 (Apr. 13, 2007).
Savran, et al., "Fabrication and Characterization of a Micromechanical Sensor for Differential Detection of Nanoscale Motions," *Journal of Microelectromechanical Systems* 11(6):703-708 (Dec. 2002).
Soderquist, Office Action U.S. Appl. No. 10/967,748 (Feb. 27, 2007).
Sulchek, et al., "Dual Integrated Actuators for Extended Range High Speed Atomic Force Microscopy," *Applied Physics Letters* 75(11):1637-1639 (Sep. 13, 1999).
Tortonese, et al., "Characterization of Application Specific Probes for SPMs," *Proceedings SPIE* 3009:53-60 (Apr. 1997).
Wolf, et al., "Temperature Dependence of the Piezoelectric Response in Lead Zirconate Titanate Films," *Journal of Applied Physics* 95(3):1397-1406 (Feb. 1, 2004).
Yasumura, et al., "Quality Factors in Micron- and Submicron-Thick Cantilevers," *Journal of Microelectricalmechanical Systems* 9(1):117-125 (Mar. 2000).
Yazdi, et al., "Micromachined Inertial Sensors," *Proceedings of the IEEE* 86(8):16401659 (Aug. 1998).
Abedinov, et al., "Micromachined Piezoresistive Cantilever Array with Integrated Resistive Microheater for Calorimetry and Mass Detection," *Journal of Vacuum & Science Technology* 19(6); pp. 2884-2888 (Nov./Dec. 2001).
Adams, "Scanning Probe Microscope Development, MEMS, and Nanotechnology," *Nevada Ventures in Nanoscience Program Presentation*; pp. 1-27 (Aug. 12, 2002).
Adams, et al., "Nanowatt Chemical Vapor Detection With a Self-Sensing, Piezoelectric Microcantilever Array," *Applied Physics Letters*, vol. 83, No. 16, pp. 3428-3430 (Oct. 20, 2003).
Adams, et al., "Self-Sensing Tapping Mode Atomic Force Microscopy," *Sensors and Actuators*, vol. A 121, pp. 262-266 (Feb. 16, 2005).
Ali, et al. , "Organic Vapour Sensing Using a Coated Piezoelectric Quartz Crystal Sensor Array," *SPIE* 3853; pp. 116-120 (Sep. 1999).
Alper, "Chemical Engineering at the Nanoscale," *NCI Alliance for Nanotechnology in Cancer*; pp. 1-4 (May 2005).
Baborowski, "Microfabrication of Piezoelectric MEMS," *Swiss Center for Electronics and Microtechnology*; pp. 1-55 (Oct. 7-8, 2004).
Barko, et al., "Application of Fuzzy Clustering and Piezoelectric Chemical Sensor Array for Investigation on Organic Compounds," *Analytica Chemica Acta* 398:219-226 (1999).
Barnes, et al., "A Femtojoule Calorimeter Using Micromechanical Sensors," *Rev. Sci. Instrum*, vol. 65, No. 12:3793-3798 (Dec. 1994).
Baselt et al., "Biosensor Based on Force Microscope Technology," *J. Vac .Sci. Technol. B* 14(2):789-793, (Mar./Apr. 1996).
Battiston et al., "A Chemical Sensor Based on a Microfabricated Cantilever array With Simultaneous Resonance-frequency and Bending Readout," *Sensors and Actuators B*, 77:122-131 (2001).
Berger, et al., "Micromechanical Thermogravimetry," *Chemical Physics Letters*, vol. 294:363-369 (Sep. 18, 1998).
Berger, et al., "Micromechanics: A Toolbox for Femtoscale Science: Towards a Laboratory on a Tip," *Microelectronic Engineering*, vol. 35:373 (1997).
Berger et al., "Transduction Principles and Integration of Chemical Sensors into a Micromechanical Array Device," *IBM Research Division Research Report*, (Dec. 1997).
Blick et al., "Nanostructured Silicon for Studying Fundamental Aspects of Nanomechanics," *Journal of Physics* CM 14:R905-R945 (2002).
Braun et al., "Micromechanical Mass Sensors for Biomolecular Detection in a Physiological Environment," *Physical Review* 72(3):031907(9) (2005).
Britton, C.L. Jr. et al, "Multiple-Input Microcantilever Sensors" *Ultramicroscopy* 82, pp. 17-21 (2000).
Bruckner et al., "Piezoelektrisch Gekoppelte Integrierbare Nanoelektromechannische Sensorschaltungen" *Integrierte elllekktrokeramische Funktionsstrukkturen*; pp. 1-20, (Sep. 28-29, 2004).

Buck, et al, "Piezoelectric Chemical Sensors," *Pure Appl. Chem.* 76(6):1139-1160 (2004).

Burg et al., "Suspended Microchannel Resonators for Biomolecular Detection," *Applied Physics Letters* 83(13):2698-2700 (Sep. 29, 2003).

Campbell et al., "Detection and Quantification of Proteins Using Self-Excited PZT-Glass Millimeter-Sized Cantilever," *Biosensors and Bioelectronics* 21:597-607 (Jan. 22, 2005).

Cavicchi, et al., "Micro-differential scanning calorimeter for combustible gas sensing," *Sensors and Actuators*, vol. B 97, pp. 22-30 (2004).

Chen et al., "Resonance Response of Scanning Force Microscopy Cantilevers," *Rev. Sci. Instrum.* 65(8): 2532-2537 (Aug. 1994).

Chen et al., "Adsorption-Induced Surface Stress and its Effects on Resonance Frequency of Microcantilevers," *J. Appl. Phys.* 77(8):3618-3622 (Apr. 15, 1995).

Cherian et al., "Determination of Adsorption-Induced Variation in the Spring Constant of a Microcantilever," *Applied Physics Letters* 80 (12):2219-2221 (Mar. 25, 2002).

Chu et al., "Novel High Vacuum Scanning Force Microscope Using a Piezoelectric Cantilever and the Phase Detection Method," *J. Vac . Sci . Technol. B* 15(4):1551-1555 (Jul./Aug. 1997).

Chu et al., "Frequency Modulation Detection High Vacuum Scanning Force Microscope With a Self-Oscillating Piezoelectric Cantilever," *J. Vac. Sci. Technol. B* 15(5):1647-1651 (Sep./Oct. 1997).

Chu et al., "Tip-Scanning Dynamic Force Microscope Using Piezoelectric Cantilever for Full Wafer Inspection," *Jpn .J. Appl. Phys.* 38(Part 1, No. 123):7155-7158 (Dec. 1999).

Cleland, "Single-Crystal Aluminum Nitride Nanomechanical Resonators," *Applied Physics Letters* 79(13):2070-2072 (Sep. 24, 2001).

Datskos, et al., "Chemical Sensors Based on Nanomechanical Resonators," *CalSpec factsheet*, OakRidge National Laboratory.

Datskos, et al., "Micro and Nanocantilever Sensors," *Encyclopedia of Nanoscience and Nanotechnology* X; pp. 1-10 (2004).

Datskos, et al., "Detection of Chemical, Biological and Radiological Stimuli Using Nanosensor Arrays," *CalSpec factsheet*, OakRidge National Laboratory.

Datskos, et al., "MEMS Based Calorimetric Spectroscopy," *CalSpec factsheet*, OakRidge National Laboratory.

Datskos, et al., "Nanocantilever Signal Transduction by Electron Transfer," *Journal of Nanoscience and Nanotechnology*, vol. 2., No. 3/4: pp. 369-373 (2002).

Davis, et al., "Fabrication and Characterization of Nanoresonating Devices for Mass Detection," *Journal of Vacuum & Science Technology*, 18(2); pp. 612-616 (Mar./Apr. 2000).

DeVoe, et al., "Modeling and Optimal Design of Piezoelectric Cantilever Microactuators," *JMEMS*, vol. 6(3): pp. 266-270 (Sep. 1997).

DeVoe, "Piezoelectric Thin Film Micromechanical Beam Resonators," *Sensors and Actuators* A(88):263-272, (2001).

DeVoe, "Thin Film Zinc Oxide Microsensors and Microactuators," *Ph.D. Dissertation*, University of California, Berkeley (1997).

Dohn et al., "Enhanced Functionality of Cantilever Based Mass Using Higher Modes," Applied Physics Letters 86:233501-3 (Jun. 3, 2005).

Ekinci, "Ultimate Limits to Inertial Mass Sensing Based Upon Nanoelectromechanical Systems," *Journal of Applied Physics* 95(5):2682-2689 (Mar. 1, 2004).

Ekinci et al, "Nanoelectromechanical Systems," *Review of Scientific Instruments* 76:061101-1 (May 26, 2005).

Fabian, et al., "Micromechanical Thermograimetry on Single Zeolite Crystals," *IBM Research Report*, vol. RZ 3047, (93093) 4 pages (Aug. 17, 1998).

Fadel et al., "Signal-to-Noise Ratio of Resonant Microcantilever Type Chemical Sensors as a Function of Resonant Frequency and Quality Factor," *Sensors and Actuators B* 102:73-77 (Jan. 23, 2004).

Fannin, "Design of an Analog Adaptive Piezoelectric Sensoriactuator," *MS Thesis Virginia Polytechnic Institute and State University* 1-81 (Feb. 26, 1997).

Ferrari, et al., "Resonant Piezo-Layers in Thick Film Technology Applied to Gravimetric Chemical Sensing," *Sensors and Microsystems: Proceedings of the First National Conference on Sensors and Microsystems AISEM*, Roma, World Scientific Publishing, Singapore, 271-275 (Feb. 19-20, 1996).

Foerster, et al., "Processing of Novel SiC and group III-Nitride Based Micro and Nanomechanical Devices," *Phys. Stat. Sol. A* 202(4):671-676 (2005).

Forster et al., "Project π-NEMS, DFG-SPP 1157," *Präsentation Status Meeting*, (2004).

Fon et al., "Nanoscale, Phonon-Coupled Calorimetry with Sub-Attojoule/Kelvin Resolution," *Nano Letters* 5(10):1968-1971 (2005).

Fujii et al., "Feedback Positioning Cantilever Using Lead Zirconate Titanate Thin Film for Force Microscopy Observation of Micropattern," *Applied Physics Letters* 68(4):467-468 (Jan. 22, 1996).

Grate, et al., "Hybrid Organic/Inorganic Copolymers with Strongly Hydrogen-Bond Acidic Properties for Acoustic Wave and Optical Sensors," *Chem. Mater.* 9:1201-1207 (1997).

Grate, et al., "Hydrogen Bond Acidic Polymers for Surface Acoustic Wave Vapor Sensors and Arrays," *Anal. Chem.* 71151:1033-1040 (Jan. 27, 1999).

Guan, S., "Frequency Encoding of Resonant Mass Sensors for Chemical Vapor Detection" *Analytical Chemistry*, 75 (17), pp. 4551-4557 (Jul. 17, 2003).

Gupta, et al., "Single Virus Particle Mass Detection Using Microresonators with Nanoscale Thickness," *Applied Physics Letters* 84(11):1976-1978 (Mar. 15, 2004).

Horowitz et al., "Design and Characterization of a Micromachined Piezoelectric Microphone," *11th AIAA/CEAS Aeroacoustics Conference* 2005 (May 23-25, 2005).

Huang et al., "VHF/UHF and Microwave Frequency Nanomechanical Resonators," *New Journal of Physics* 7 (247):1-15, (Nov. 29, 2005).

Hughes, "A Microfabricated Piezoelectric Cantilever Beam Biosensor," *Ph.D. Dissertation University of Minnesota*, (Aug. 1999).

Indermuhle et al., "Self-Sharpening Tip Integrated on Micro Cantilevers With Self-Exciting Piezoelectric Sensor for Parallel Atomic Force Microscopy," *Applied Physics Letters* 70(17):2318-2320 (Apr. 28, 1997).

Itoh et al., "Development of a Force Sensor for Atomic Force Microscopy Using Piezoelectric Thin Films," *Nanotechnology* 4:218-224 (1993).

Itoh et al., "Force Sensing Microcantilever Using Sputtered Zinc Oxide Thin Film," *Appl. Phys. Lett.* 64(1):37-39 (Jan. 3, 1994).

Itoh et al., "Deflection Detection and Feedback Actuation Using a Self-Excited Piezoelectric Pb(Zr,Ti)O$_3$ Microcantilever for Dynamic Scanning Force Microscopy," *Applied Physics Letters* 69(14):2036-2038 (Sep. 30, 1996).

Itoh et al., "Self-Excited Force-Sensing Microcantilevers with Piezoelectric Thin Films for Dynamic Scanning Force Microscopy," *Sensors and Actuators A* 54:477-481 (1996).

Itoh et al., "Piezoelectric Sensor for Detecting Force Gradients in Atomic Force Microscopy," *Jpn. J. Appl. Phys.* 33(Part 1, 1A):334-340 (Jan. 2004).

Jain et al., "A Microheater Device for Study of Temperature Gradient Effects on Neurite Outgrowth in Retinal Ganglion Cells," *ARVO Annual Meeting 2004*, Ft. Lauderdale, FL, (Apr. 25-28, 2004).

Johnson, "Characterization of Piezoelectric ZnO Thin Films and the Fabrication of Piezoelectric Micro-Cantilevers" *Thesis, Iowa State University* ; pp. 1-98 (2005).

Kim et al., "Multicomponent Analysis and Prediction with a Cantilever Array Based Gas Sensor," *Sensors and Actuators B* 78:12-18 (2001).

Kong, et al. "A MEMS Sensor Array for Explosive Particle Detection," *IEEE Proceedings of 2004 International Conference on Information Acquisition*; pp. 278-281 (2004).

Kunt, et al., "Optimization of Temperature Programmed Sensing for Gas Identification Using Micro-Hotplate Sensors," *Sensors and Actuators B* 53:24-43 (1998).

Lange, et al., "Complimentary Metal Oxide Semiconductor Cantilever Arrays on a Single Chip: Mass-Sensitive Detection of Volatile Organic Compounds," *Anal. Chem.* 74 (13):3084-3095 (Jul. 1, 2002).

Lang, et al. "Nanomechanics from Atomic Resolution to Molecular Recognition Based on Atomic Force Microscopy Technology," *Nanotechnology* 13: R29-R36 (Sep. 25, 2002).

Lange, D. et al, "CMOS Resonant Beam Gas Sensing System With On-Chip Self Excitation", *IEEE International Conference on Micro Electro Mechanical Systems*, Technical Digest (14) 547-552, (Jan. 21-25, 2001).

Lang et al., "The Nanomechanical NOSE," *Chem. Phys. Lett.* 217:589-594 (1994).

Lavrik, et al., "Cantilever Transducers as a Platform for Chemical and Biological Sensors," *Review of Scientific Instruments*, vol. 75, (7); pp. 2229-2253 (Jan. 2004).

Lee, C. et al, Technical Digest—International Electron Devices Meeting, 545-548 (1996).

Lee, et al., "Microcantilevers Integrated With Heaters and Piezoelectric Detectors for Nano Data-Storage Application," *Applied Physics Letters*, 83, (23), 4839-4841 (Dec. 8, 2003).

Lee, et al., "Self-Excited Piezoelectric Cantilever Oscillators," *Sensors and Actuators*, A 52, 41-45 (1996).

Lee, International Search Report Regarding PCT/US2005/035216 (Aug. 28, 2006).

Lee et al., "Characterization of Micromachined Piezoelectric PZT Force Sensors for Dynamic Scanning Force Microscopy," *Rev. Sci. Instrum.* 68(5):2091-2100 (May 1997).

Lee et al., "Development of a Piezoelectric Self-Excitation and Self-Detection Mechanism in PZT Microcantilevers for Dynamic Scanning Force Microscopy in Liquid," *J. Vac. Sci. Technol. B* 15(4):1559-1563 (Jul./Aug. 1997).

Lee et al., "Piezoelectric Cantilever Acoustic Transducer," *J. Micromech. Microeng.* 8:230-238 (1998).

Lee et al., "Self-Excited Piezoelectric PZT Microcantilevers for Dynamic SFM—with Inherent Sensing and Actuating Capabilities," *Sensors and Actuators A* 72:179-188 (1999).

Lee, et al., "Smart Force Sensors for Scanning Force Microscope Using the Micromachined Piezoelectric PZT Cantilevers," *IEEE International Electronic Devices Meeting*, San Francisco CA 20.7.1-20.7.4 (Aug. 1, 1996).

Li et al., "Electromechanical Behavior of PZT-Brass Unimorphs," *J. Am. Ceram. Soc.* 82(7):1733-1740 (1999).

Llic, et al., "Attogram Detection Using Nanoelectromechanical Oscillators," *Journal of Applied Physics* 95(7):3694-3703 (Apr. 1, 2004).

Madden et al., "Conducting Polymer Sensors for the Home," Publication Source and Publication Date Unknown.

Manning, et al., "Self-Oscillating Tapping Mode Atomic Force Microscopy," *Review of Scientific Instruments*, 74 (9): 4220-4222 (Sep. 2003).

Marie, R. et al, "Adsorption Kinetics and Mechanical Properties of Thiol-Modified DNA-Oligos on Gold Investigated by Microcantilever Sensors" Ultramicroscopy, 91, 29-36 (2002).

Martin et al., "Isothermal Measurements and Thermal Desorption of Organic Vapors Using SAW Devices," *IEEE Transactions on Ultrasonics, Ferroelectrics, and Frequency Control* 34(2):142-147 (Mar. 1987).

Mehta et al., "Manipulation and Controlled Amplification of Brownian Motion of Microcantilever Sensors," *Applied Physics Letters* 78(11):1637-1639 (Mar. 12, 2001).

Miller et al., "A MEMS Radio-Frequency Ion Mobility Spectrometer for Chemical Agent Detection (abstract)," *Proceedings of the 2000 Solid-State Sensor and Actuator Workshop, Hilton Head Island, SC* 36-43 (Jun. 4-8, 2000).

Minne et al., "Contact imaging in the Atomic Force Microscope Using a Higher Order Flexural Mode Combined With a New Sensor," *Applied Physics Letters* 68(10):1427-1429 (Mar. 4, 1996).

Miyahara et al., "Lead Zirconate Titanate Cantilever for Noncontact Atomic Force Microscopy," *Applied Surface Science* 140:428-431 (1999).

Miyahara et al., "Non-Contact Atomic Force Microscope with a PZT Cantilever Used for Deflection Sensing, Direct Oscillation and Feedback Actuation," *Applied Surface Science* 188:450-455 (2002).

Moriizumi, T. et al, "Multi-Channel Saw Chemical Sensor Using 90Mhz Saw Resonator and Partial Casting Molecular Films" Proceedings—IEEE Ultrasonics Symposium, 449-502 (1994).

Muralidharan et al., "Absorption-Desorption of Explosive Vapors Investigated With Microcantilevers," *Ultramicroscopy* 97:433-439 (2003).

Nam, et al., "Piezoelectric PZT Cantilever Array Integrated with Piezoresistor for High Speed Operation and Calibration of Atomic Force Microscopy," *Journal of Semiconductor Technology and Science*, 2 (4): 246-252 (Dec. 2002).

Nam et al., "End Point Motion Estimation of a Cantilevered Piezoelectric Beam," *International Conference on Mechatronics and Information Technology*, Japan 215-219, (2001).

Oden, "Gravimetric Sensing of Metallic Deposits Using an End-Loaded Microfabricated Beam Structure," *Sensors and Actuators B* 53:191-196 (1998).

Paci et al., "A Behavioural Model of Resonant Cantilevers for Chemical Sensing," *Analog Integrated Circuits and Signal Processing* 44:119-128 (2005).

Passian et al., "Dynamics of Self-Driven Microcantilevers," *Journal of Applied Physics* 91(7):4693-4700 (Apr. 1, 2002).

Piekaraski et al., "Surface Micromachined Piezoelectric Resonant Beam Filters," *Sensors and Actuators* A 90(3):313-20 (2001).

Pinnaduwage, et al., "A Microsensor for Trinitrotoluene Vapour," *Nature*, 425: 474 (Oct. 2, 2003).

Pinnaduwage et al. "Sensitive Detection of Plastic Explosives with Self-Assembled Monolayer-Coated Microcantilevers," *Applied Physics Letters* 83(7):1471-1473 (Aug. 18, 2003).

Pinnaduwage et al., "Adsorption of Trinitrotoluene on Uncoated Silicon Microcantilever Surfaces," *Langmuir* 20 (7):2690-2694 (2004).

Pinnaduwage et al., "Detection of 2, 4-Dinitrotoluene Using Microcantilever Sensors," *Sensors and Actuators B* 1-72 (2004).

Pinnaduwage et al., "Moore's Law in Homeland Defense—An Integrated Sensor Platform Based on Silicon Micro Cantilevers," *IEEE Sensors Journal* 5(4)774-785 (Aug. 2005).

Polla et al., "Processing and Characterization of Piezoelectric Materials and Integration into Microelectromechanical Systems," *Annu. Rev. Mater. Sci.* 28:563-597 (1998).

Polla, et al., "Integrated Multi-Sensor Chip," *IEEE Electron Device Letters* EDL-7 (4): 254-256 (Apr. 1986).

Porter, T.L. et al, "Sensor Based on Piezoresistive Microcantilever Technology" *Sensors and Actuators* A, 88, 47-51 (2001).

Postma et al., "Dynamic Range of Nanotube- and Nanowire-Based Electromechanical Systems," *Applied Physics Letters* 86:223105-3 (May 25, 2005).

Pozidis et al., "Demonstration of Thermomechanical Recording at 641 Gbit/in$^2$," *IEEE Transactions on Magnetics* 40(4):2531-2536 (Jul. 2004).

Reevis, Office Action Regarding U.S. Appl. No. 11/089,559 (Jul. 22, 2005).

Reevis, Office Action Regarding U.S. Appl. No. 11/089,559 (Oct. 13, 2005).

Reevis, Office Action Regarding U.S. Appl. No. 11/089,559 (May 11, 2006).

Rogers, et al., "Mercury Vapor Detection with a Self-Sensing, Resonating Piezoelectric Cantilever," *Review of Scientific Instruments*, 74(11): 4899-4901 (Nov. 2003).

Rogers et al., "Improving Tapping Mode Atomic Force Microscopy with Piezoelectric Cantilevers," *Ultramicroscopy* 100:267-276 (2004).

Ruby "FBAR—From Technology Development to Production," *Second International Symposium on Acoustic Wave Devices for Future Mobile Communications Systems*, (Mar. 2005).

Sandberg, et al., "Temperature and Pressure Dependence of Resonance in Multi-Layer Microcantilevers," *Journal of Micromechanics and Microengineering* 15:1454-1458 (Jun. 6, 2005).

Semanick et al., "Microhotplate Platforms for Chemical Sensor Research," *Sensors and Actuators B* 77:579-591 (2001).

Sepaniack, et al., "Microcantilever Transducers:A New Approach in Sensor Technology," *Analytical Chemistry* 568A-575A (Nov. 1, 2002).

Sharos et al., "Enhanced Mass Sensing Using Torsional and Lateral Resonances in Microcantilevers," *Applied Physics Letters* 84(23):4638-4640 (Jun. 7, 2004).

Shibata et al., "Characterization of Sputtered ZnO Thin Film as Sensor and Actuator for Diamond Afm Probe," *Sensors and Actuators A* 102:106-113 (2002).

Shih et al., "Simultaneous Liquid Viscosity Density Determination with Piezoelectric Unimorph Cantilevers," *Journal of Applied Physics* 89(2):1497-1505 (Jan. 15, 2001).

Shin, et al. "Fabrication and Sensing Behavior of Piezoelectric Microcantilever for Nanobalance," *Japanese Journal of Applied Physics* 42 (Part 1 No. 9B): 6139-6142 (2003).

Soderquist, Office Action Regarding U.S. Appl. No. 10/967,748 (May 24, 2006).

Soderquist, Office Action Regarding U.S. Appl. No. 10/967,748 (Oct. 4, 2005).

Soderquist, Office Action Regarding U.S. Appl. No. 10/967,748 (Mar. 10, 2005).

Su et al., "Microcantilever Resonance-Based DNA Detection with Nanoparticle Probes," *Applied Physics Letters* 82(20):3562-3564 (May 19, 2003).

Suehira et al., "Development of Low Temperature Ultrahigh Vacuum Noncontact Atomic Force Microscope with PZT Cantilever," *Applied Surface Science* 157:343-348 (2000).

Suehle, et al., "Tin Oxide Gas Sensor Fabricated Using CMOS Micro-Hotplates and In-Situ Processing," *IEEE Electronic Device Letters* 14(3):118-120 (Mar. 1993).

Sulchek, et al., "Dual Integrated Actuators for Extended Range High Speed Atomic Force Microscopy," *Applied Physics Letters*, 75 (11): 1637-1639 (Sep. 13, 1999).

Tamayo et al., "Chemical Sensors and Biosensors in Liquid Environment Based on Microcantilevers with Amplified Quality Factor," *Ultramicroscopy* 0:1-7 (2001).

Tani et al., "Effectiveness and Limits of Self-Sensing Piezoelectric Actuators" *International Workshop on Structural Health Monitoring Stanford University* 502-514 (Sep. 18-20, 1997).

Tatsuma, T. et al, "Multichannel Quartz Crystal Microbalance" *Analytical Chemistry*, 71 (17): 3632-3636 (Sep. 1999).

Thundat et al., "Thermal and Ambient-Induced Deflections of Scanning Force Microscope Cantilevers," *Appl. Phys. Lett.* 64(21):2894-2896 (May 23, 1994).

Thundat et al., "Detection of Mercury Vapor Using Resonating Microcantilevers," *Applied Physics Letters* 66(13):1695-1697 (Mar. 27, 1995).

Voiculescu et al., "Electrostatically Actuated Resonant Microcantilever Beam in CMOS Technology for the Detection of Chemical Weapons," *IEEE Sensors Journal* 5(4):641-647 (Aug. 2005).

Wang et al., "Theoretical Analysis of the Sensor Effect of Cantilever Piezoelectric Benders," *Journal of Applied Physics* 85(3):1702-1712 (Feb. 1, 1999).

Watanabe et al., "Micro-Fabricated Piezoelectric Cantilever for Atomic Force Microscopy," *Rev .Sci. Instrum.* 67(11):3898-3903 (Nov. 1996).

Weigert et al., "Frequency Shifts of Cantilevers Vibrating in Various Media," *Applied Physics Letters* 69(19):2834-2836 (Nov. 4, 1996).

Weinberg, "Working Equations for Piezoelectric Actuators and Sensors," *ASME/IEEE Journal of MEMS* 8(4):71-78 (1999).

Wright, "Fabrication and Testing of Heated Atomic Force Microscope Cantilevers," *Georgia Institute of Technology Thesis* 1-111 (May 2005).

Yang et al., "Mechanical Behavior of Ultrathin Microcantilever," *Sensors and Actuators* 82:102-107, 2000.

Yi, et al., "In Situ Cell Detection Using Piezoelectric Lead Zirconate Titanate-Stainless Steel Cantilevers," *J. Applied Physics* 93 (1): 619-625 (Jan. 1, 2003).

Yi, et al., "Effect of Length, Width, and Mode on the Mass Detection Sensitivity of Piezoelectric Unimorph Cantilevers," *J. Applied Physics* 91 (3): 1680-1686 (Feb. 1, 2002).

Yue et al., "Cantilever Arrays for Multiplexed Mechanical Analysis of Biomolecular Reactions," *MCB* 1(3):211-220 (2004).

Zhang et al., "Tuning Forks as Micromechanical Mass Sensitive Sensors for Bio- or Liquid Detection," *Sensors and Actuators B* 94:65-72 (2003).

Zhang et al., "Frequency-Tuning for Control of Parametrically Resonant Mass Sensors," *J. Vac. Sci .Technol. A* 23(4):1-5 (Jul./Aug. 2005).

Zhou, J. et al, "Self-Excited Piezoelectric Microcantilever for Gas Detection" *Microelectronic Engineering*, 69, 37-46 (2003).

Jones, Examination Report under Section 18(3) for British Application No. BG0609690.3, 4 pp. (Jan. 14, 2008).

Phipps, Examination Report under Section 18(3) for British Application No. GB0708212.6, 3 pp., Apr. 2, 2008.

Official Action issued in U.S. Appl. No. 12/416,852, mailed on Jun. 11, 2010.

Official Action issued in U.S. Appl. No. 12/416,852, mailed on Dec. 21, 2010.

Official Action issued in U.S. Appl. No. 12/416,852, mailed on Jun. 3, 2011.

Official Action issued in U.S. Appl. No. 11/845,680, mailed Dec. 10, 2010.

Official Action issued in U.S. Appl. No. 11/845,680, mailed Jul. 18, 2011.

Official Action issued in U.S. Appl. No. 11/845,661, mailed on Sep. 23, 2010.

Official Action issued in U.S. Appl. No. 11/845,661, mailed on Mar. 22, 2011.

Notice of Allowance issued in U.S. Appl. No. 11/845,661, dated Oct. 22, 2010.

Notice of Allowance issued in U.S. Appl. No. 11/845,661, dated Jul. 6, 2011.

Muro H. et al., Semiconductor or Vibration Sensors Using Multiple Cantilever Beams with Different Lengths, Electronics and Communications in Japan, Part 2, 1991, pp. 109-116, vol. 74, No. 8.

Amrani, M. E. H. et al., Multi-frequency interrogation technique applied to conducting polymer gas and odour sensors, IEE Proceedings—Science, Measurement and Technology, Mar. 1999, pp. 95-101, vol. 146, No. 2.

Maute, M. et al., Fabrication and application of polymer coated cantilevers as gas sensors, Microelectronic Engineering, 1999, pp. 439-442, vol. 46.

Maute, M. et al., Detection of volatile organic compounds (VOC's) with polymer-coated cantilevers, Sensors and Actuators B Chemical, 1999, pp. 505-511, vol. 58.

Keefe, M. H. et al., Mesoporous Thin Films of "Molecular Squares" as Sensors for Volatile Organic Compounds, Langmuir, 2000, pp. 3694-3970, vol. 16.

Kim, B.H. et al., Parallel Frequency Readout of an Array of Mass-Sensitive Tranducers for Sensor Applications, Microelectronic Engineering, 2000, pp. 229-232, vol. 53.

Zambov, L. M. et al., Gas-Sensitive Properties of Nitrogen-Rich Carbon Nitride Films, Advanced Materials, 2000, pp. 656-600, vol. 12, No. 9.

Hagleitner, C. et al., CMOS Single-Chip Multisensor Gas Detection System, The Fifteenth IEEE International Conference on Micro Electro Mechanical Systems, Las Vegas, NV, 2002, pp. 244-247, vol. 2, No. 2.

Djuric, Z. et al. Influence of Adsorption-Desorption Process on Resonant Frequency and Noice of Micro- and Nanocantilevers, 23rd International Conference on Microelectronics, 2002, pp. 243-246, vol. 1.

Belaubre, P. et al., Fabrication of biological microarrays using microcantilevers, Applied Physics Letters, 2003, pp. 3122-3124, vol. 82, No. 18.

Advisory Action issued in U.S. Appl. No. 11/845,680, mailed Oct. 3, 2011, 3 pages.

Official Action issued in U.S. Appl. No. 11/845,661, mailed Oct. 4, 2011, 12 pages.

\* cited by examiner

CANTILEVERED PROBE DETECTOR WITH PIEZOELECTRIC ELEMENT

CROSS-REFERENCE TO RELATED APPLICATIONS

This application is a continuation of U.S. patent application Ser. No. 11/845,661, now U.S. Pat. No. 8,136,385, filed Aug. 27, 2007, which is a continuation of U.S. patent application Ser. No. 11/576,443, now U.S. Pat. No. 7,694,346, filed Mar. 30, 2007, which is the U.S. National Stage of International Application No. PCT/US2005/035216, filed Sep. 30, 2005, which was published in English under PCT Article 21(2), which in turn claims the benefit of the earlier filing date of U.S. Provisional Application No. 60/614,592, filed Oct. 1, 2004, each of which is hereby incorporated by reference in its entirety. This application is related to U.S. Ser. No. 13/350,921, filed Jan. 16, 2012, U.S. Ser. No. 13/417,939, filed Mar. 12, 2012, and U.S. Ser. No. 12/416,852, filed Apr. 1, 2009.

ACKNOWLEDGMENT OF GOVERNMENT SUPPORT

This invention was made with Government support under Prime Contract No. DE-AC05-00OR22725 awarded to UT-Battelle, LLC, by the U.S. Department of Energy and a subcontract awarded to the University of Nevada, Reno by UT-Battelle, LLC. The Government may have certain rights in this invention.

FIELD

This disclosure relates generally to chemical detection, and more particularly to systems and methods for sensing target materials, such as explosive materials, using cantilevered probes.

BACKGROUND

The burgeoning market for explosives screening equipment and an increase in research on chemical and explosive detection technologies are in response to the greater need to perform real-time detection of undesirable chemicals and hidden explosives, such as those concealed in luggage, shipping containers, land mines, and unexploded ordinances. The market for devices that screen people for explosives and various types of biological, chemical or nuclear/radiological weapons is estimated by Homeland Security Research Corp. to reach $3.5 billion by 2006 and $9.9 billion by 2010.

Among the wide range of materials from which explosives can be made are organic nitrates, organonitro compounds, ketone and acyl peroxides, inorganic chlorates, perchlorates, nitrates, fulminates, and acetylides. Some of the explosive residue chemical compounds for detection and identification include 2,4,6-trinitrotoluene (TNT), 2,4,6,n-tetranitro-n-methylaniline (Tetryl), 1,3,5-trinitro-1,3,5-triazacyclohexane (RDX), 1,3,5,7-tetranitro-1,3,5,7-tetrazacyclooctane (HMX), pentaerythritol tetranitrate (PETN), glycerol trinitrate (nitroglycerin), and ethylene glycol dinitrate (EGDN).

Many obstacles remain for scientists and engineers working to develop equipment and processes for detecting explosives. Dogs continue to be the preferred explosive detectors, yet widespread deployment of canine teams is neither practical nor cost effective. Moreover, currently available non-canine explosive sensor equipment tends to be complex, bulky, and expensive, and cannot be miniaturized easily.

Currently available explosive and bomb detection systems typically absorb particulate or vapor matter onto a surface, and analyze the matter using techniques such as ion mobility spectrometry (IMS), mass spectroscopy, nuclear magnetic resonance analysis, and gas chromatography. Successful explosive and chemical detection techniques can require sensitivity as low as parts per trillion to parts per quadrillion, in that small explosive devices such as anti-personnel land mines may be constructed from plastic and other non-metallic substances having low vapor pressures. One exemplary explosive and chemical detection system used in airports exposes luggage to a stream of air that dislodges chemicals into the air as vapors, which are subsequently concentrated to create detectable levels of the chemicals. Unfortunately, many conventional explosive and chemical detection systems still have high false alarm rates, slow throughput, operator dependences, and high transaction costs.

Some conventional explosive detection systems include cantilevered elements. One example of this type of system is described by Thundat in "Microcantilever Detector for Explosives," U.S. Pat. No. 5,918,263, issued Jun. 29, 1999 (Thundat). As disclosed in Thundat, explosive gas molecules that have been adsorbed onto a microcantilever are subsequently heated to cause combustion, which in turn causes bending and a transient resonance response of the microcantilever. Movement of the microcantilever is detected by a laser diode, which is focused on the microcantilever, and a photodetector, which detects deflection of the reflected laser beam caused by a heat-induced deflection and resonance response of the microcantilever. Conventional explosive detectors that include cantilevered elements, such as the detector disclosed in Thundat, have a variety of limitations. For example, many such detectors cannot be miniaturized because they require external cantilever actuation and external sensing.

SUMMARY

Disclosed herein are embodiments of a chemical detection system for detecting a target material, such as an explosive material. Some of these embodiments have potential as extremely sensitive yet inexpensive sensors that can be mass-produced, thereby enabling large-scale sensor deployment. For example, some embodiments may offer several orders of magnitude greater sensitivities when compared to other micro-electrical-mechanical systems (MEMS) such as quartz crystal microbalances (QCM), flexural plate wave oscillators (FPW), and surface acoustic wave devices (SAW).

Embodiments of the disclosed chemical detection system can include, for example, a cantilevered probe, a probe heater thermally coupled to the cantilevered probe, and a piezoelectric element disposed on the cantilevered probe. The piezoelectric element can be configured to detect the target material by a variety of processes, such as by detecting bending, vibrations, recoil, or other movements of the cantilevered probe, a temperature change of the cantilevered probe, an impedance shift of the cantilevered probe, or a resonant frequency shift of the cantilevered probe. In some embodiments, the piezoelectric element is configured to actuate movement of the cantilevered probe. This movement can be useful in the detection process, such as to detect a resonant frequency shift of the cantilevered probe.

The piezoelectric element can include a piezoelectric film disposed on a surface of the cantilevered probe. In some embodiments, the piezoelectric element comprises zinc oxide, lead zirconate titanate, aluminum nitride, a piezoelectric material, or a derivative or combination thereof. The piezoelectric element also can comprise a pyroelectric material. In some embodiments, the probe heater includes piezoresistive element formed in the cantilevered probe, a heater element disposed on the cantilevered probe, or both.

Embodiments of the disclosed chemical detection system can include a variety of additional elements. Some embodiments include an interface circuit electrically coupled to the piezoelectric element. For example, some embodiments include an interface circuit comprising the piezoelectric element as a bridge element in an AC bridge circuit. This AC bridge can be tuned, for example, to one of an on-resonance condition or an off-resonance condition to detect the target material. Embodiments of the disclosed chemical detection system also can include a thermally conductive mesh substantially surrounding the cantilevered probe. This can be useful, for example, to limit the egression of thermal energy liberated by exothermic reactions, such as the deflagration of explosive materials. Embodiments of the disclosed chemical detection system also can include a mechanical stop configured to contact the cantilevered probe. This stop can be used, for example, to detect movement of the cantilevered probe. Some embodiments are handheld. These and other embodiments can include an enclosure, such as a handheld enclosure.

Examples of target materials that can be detected by some embodiments of the disclosed chemical detection system include 2,4,6-trinitrotoluene, 2,4,6,n-tetranitro-n-methylaniline, 1,3,5-trinitro-1,3,5-triazacyclohexane, 1,3,5,7-tetranitro-1,3,5,7-tetrazacyclooctane, pentaerythritol tetranitrate, glycerol trinitrate, ethylene glycol dinitrate, and derivatives and combinations thereof. To aid in the detection of trace concentrations, some embodiments include a target material concentrator coupled to the cantilevered probe. These and other embodiments also can include a selective coating disposed on at least a portion of the cantilevered probe, the selective coating being configured for selective adsorption of the target material. In these and other embodiments, additional selectivity can be achieved by fabricating multiple cantilevered probes in a cantilevered probe array. In these arrays, at least two of the cantilevered probes can be frequency-differentiated. For example, at least one cantilevered probe can be tuned to an on-resonance condition while at least one other cantilevered probe is tuned to an off-resonance condition. Multiple cantilevered probes in a cantilevered probe array, such as frequency-differentiated cantilevered probes, can be connected in series.

Also disclosed are embodiments of a method of detecting a target material, such as an explosive material. These embodiments can include, for example, exposing a cantilevered probe to a carrier including a target material such that the target material is transferred onto the cantilevered probe. Some embodiments also include heating the cantilevered probe, such as to a temperature sufficient to cause the target material to undergo a phase change or to a temperature sufficient to cause the target material to deflagrate or ignite. These and other embodiments also can include piezoelectrically detecting a movement of the cantilevered probe or a property of the cantilevered probe, such as by generating an electrical signal with a piezoelectric element connected to the cantilevered probe. The same or another piezoelectric element also can be used to piezoelectrically actuate a movement of the cantilevered probe. In some embodiments, piezoelectric elements are driven by a variable-frequency drive voltage, such as to isolate the responses of frequency-differentiated cantilevered probes.

In some disclosed embodiments, the movement of the cantilevered probe or a change in the property of the cantilevered probe is caused by transferring the target material onto the cantilevered probe. Some disclosed embodiments also include causing the target material to undergo a phase change or a reaction. This phase change or reaction also can cause the movement of the cantilevered probe or a change in the property of the cantilevered probe. Also among the movements and property changes that can be piezoelectrically detected are resonant frequency shifts, cantilever bending, thermal signatures, recoil responses, pyroelectric charge generation, impedance shifts and temperature shifts. Based on the movement of the cantilevered probe or a change in the property of the cantilevered probe, some embodiments also include identifying the target material. Identifying the target material can involve comparing a cantilevered probe response to a reference cantilevered probe response.

Also disclosed are embodiments of a method for making a chemical detection system. These embodiments can include providing a cantilevered probe, providing a probe heater thermally coupled to the cantilevered probe, and providing a piezoelectric element disposed on the cantilevered probe. In some of these embodiments, providing the piezoelectric element includes depositing a piezoelectric film on a surface of the cantilevered probe. These and other embodiments also can include depositing a selective coating on a surface of the cantilevered probe. More than one cantilevered probe can be assembled to form a cantilevered probe array.

Various embodiments are illustrated in part by the accompanying drawings and the detailed description given below. The drawings and the detailed description should not be taken to limit the invention to the specific embodiments, but are for explanation and understanding. Furthermore, the drawings are not drawn to scale. The drawings and the detailed description are merely illustrative of the invention rather than limiting, the scope of the invention being defined by the appended claims and equivalents thereof.

DETAILED DESCRIPTION

Figure 1:
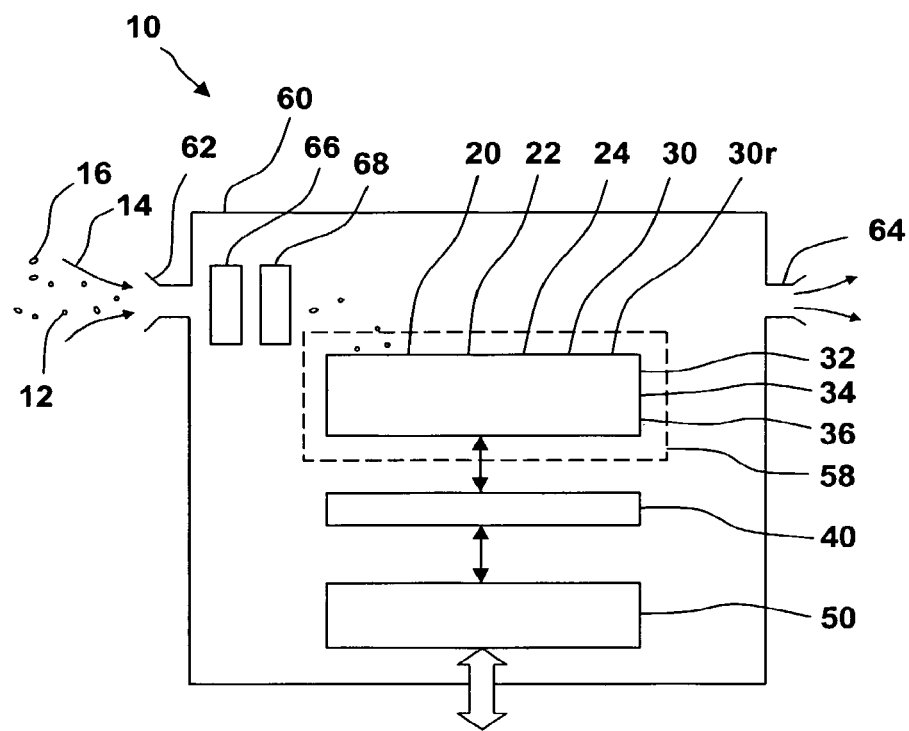
FIG. 1 is a schematic diagram of a chemical detection system for detecting at least one explosive material, in accordance with some embodiments of the current invention.

The following terms may be abbreviated in this disclosure: 1,3,5,7-tetranitro-1,3,5,7-tetrazacyclooctane (HMX), 1,3,5-trinitro-1,3,5-triazacyclohexane (RDX), 2,4,6,n-tetranitro-n-methylaniline (Tetryl), 2,4,6-trinitrotoluene (TNT), atomic force microscopy (AFM), central processing unit (CPU), deep reactive ion etching (D-RIE), digital signal processor (DSP), ethylene glycol dinitrate (EGDN), field-programmable gate array (FPGA), flexural plate wave oscillators (FPW), fast Fourier transform (FFT), glycerol trinitrate (nitroglycerin), ion mobility spectrometry (IMS), lead zircanate titinate (PZT), local area network (LAN), micro-electrical-mechanical systems (MEMS), pentaerythritol tetranitrate (PETN), quality (Q), quartz crystal microbalances (QCM), silicon-on-insulator (SOI), surface acoustic wave devices (SAW), universal serial bus (USB), and wide area network (WAN).

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. The terms "comprises" and "includes" are equivalent. The same reference numerals are used throughout the Figures to indicate similar or identical features. U.S. application Ser. No. 10/967,748 is incorporated herein by reference.

Disclosed herein are embodiments of a chemical sensor, embodiments of a method for making the disclosed chemical sensor and embodiments of a method for sensing chemicals. Although not limited by any particular advantages, the disclosed embodiments may have one or more advantages over the prior art. Some disclosed embodiments require detection surface areas that are orders of magnitude smaller than the surface areas required by other types of sensors. In addition, some embodiments are capable of operating in several detection modes, such as mass loading and bending. Most other sensors operate in only a single detection mode. Furthermore, many of the disclosed embodiments can be mass-produced at relatively low cost. For example, silicon cantilevered probes can be manufactured using standard semiconductor manufacturing equipment. Finally, some of the disclosed embodiments have demonstrated superior detection sensitivities in comparison to at least some conventional sensors.

FIG. 1 illustrates a chemical detection system 10 for detecting one or more explosive materials 16 or other target chemical species 12 also referred to as target materials, in accordance with some embodiments of the present invention. As shown, the chemical detection system 10 includes a cantilevered probe 30, a probe heater 36 thermally coupled to the cantilevered probe 30, and a piezoelectric element 32 disposed on the cantilevered probe 30. The piezoelectric element 32 can be configured to detect explosive material 16 adsorbed onto the cantilevered probe 30, such as when the probe heater 36 heats the cantilevered probe 30. In various embodiments, the piezoelectric element 32 can provide a piezoelectric element output signal related to, for example, a resonant frequency shift, cantilever bending, a thermal signature, a recoil response, a pyroelectric charge generation, an impedance shift, a temperature shift, or combinations thereof. Throughout this disclosure, descriptions of the adsorption of explosive material 16 or other target chemical species 12 refer to the attachment or inclusion of such material onto or into the cantilevered probe 30, whether by adsorption, absorption, reaction, or any other form of attachment or incorporation.

The explosive material 16 can include, for example, 2,4,6-trinitrotoluene (TNT), 2,4,6,n-tetranitro-n-methylaniline (Tetryl), 1,3,5-trinitro-1,3,5-triazacyclohexane (RDX), 1,3,5,7-tetranitro-1,3,5,7-tetrazacyclooctane (HMX), pentaerythritol tetranitrate (PETN), glycerol trinitrate (nitroglycerin), ethylene glycol dinitrate (EGDN), derivatives thereof, or combinations thereof.

The cantilevered probes 30 can be self-sensing. The chemical detection system 10 can include multiple cantilevered probes 30 arranged in a cantilevered probe array 20. Each cantilevered probe 30 can have one or more suspended cantilevered element and one or more associated piezoelectric element 32. The piezoelectric element 32 can include, for example, a deposited layer of piezoelectric material, such as zinc oxide (ZnO), lead zircanate titinate (PZT), aluminum nitride, a piezoelectric material, or a derivative or combination thereof. The piezoelectric element 32 also can include a pyroelectric material. The piezoelectric element 32 can be configured to bend, deflect or vibrate the cantilevered element when excited or actuated by an applied drive voltage. The piezoelectric element 32 also can be configured to generate a voltage as the associated cantilevered probe 30 bends, deflects or vibrates. In this way, the piezoelectric element 32 can be configured to sense movements of the associated cantilevered probe 30 such as shifts in bending, vibrations, or recoil and/or to actuate movement of the associated cantilevered probe 30. Some embodiments, however, include a separate piezoelectric drive mechanism or other mechanism that drives the cantilevered probe 30.

As mentioned above, the cantilevered probe 30 may be part of a cantilevered probe array 20. The cantilevered probes 30 in the cantilevered probe array 20 may be frequency-differentiated such that cantilevered probes having different effective masses or effective spring constants exhibit different resonant frequencies. The cantilevered probes 30 can be manufactured, for example, with small differences in cantilever lengths, resulting in separations in resonant frequencies that allow the resonant frequency of each cantilevered probe in the cantilevered probe array 20 to be detected with as few as two wires connected to the cantilevered probe array 20. Thus, the cantilevered probe arrays 20 with two or more cantilevered probes 30 can be packaged and connected to an interface circuit 40 with a minimal number of bond pads, interconnection traces and bond wires to external interface and control electronics. The interface circuit 40, which can be coupled to the cantilevered probe array 20, can be configured to actuate and sense movement of the cantilevered probes 30. Parallel arrays of cantilevered probes 30 can be configured with elements that number from a few to a million or more cantilevered probes on one substrate or die. Groups of cantilevered probe arrays 20 may be connected, for example, during on-chip trace definition, while being wire-bonded to a leadframe or package, or at the socket or board level.

Non-overlapping, independent and orthogonal explosive and chemical-sensing effects on individual cantilevered probes 30 in the cantilevered probe array 20 may be desirable but not necessary when many cantilevered probes 30 with various coatings and coating thicknesses are used for detection. Signal processing and pattern recognition of the resonance-frequency data from multiple cantilevered probes 30 may be employed to differentiate between various explosive materials and chemicals in varying concentrations having sometimes small and sometimes null effects. Differentiation between similar chemical substances can be made, and their constituency and concentration can be determined, in a system where a variety of selective coatings 34 are applied to multiple cantilevered probes 30. These selective coatings 34, for example, can be used to selectively adsorb different types of chemicals-onto the cantilevered probes 30. The selective coating 34 can be positioned on or around one or more of the cantilevered probes 30 of a cantilevered probe array 20, such as one or more cantilevered probes 30 with or without probe heaters 36, to provide, for example, two or more differentiable output signals for identifying the target chemical species 12.

The chemical detection system 10 can be configured to detect one or more target chemical species 12, such as mercury, hydrogen, an alcohol, water vapor, an explosive material, a chemical element, a chemical compound, an organic material, an inorganic material, a gaseous substance, a liquid, a biological material, a DNA strand, a bioactive agent, a toxin, or derivatives or combinations thereof. Throughout this disclosure, the target chemical species 12 can be any chemical, biological, or explosive material targeted for detection.

Typically, one or more cantilevered probes 30 can be configured to respond when exposed to the explosive material 16. For example, the cantilevered probes 30 may respond when absorbing, adsorbing, or otherwise reacting to the explosive material 16 and/or other target chemical species 12. When the cantilevered probe array 20 is exposed to the explosive material 16 and is actuated by the interface circuit 40, one or more of the cantilevered probes 30 in the cantilevered probe array 20 may exhibit a response, such as a shift in bending, a change in a resonant frequency, an impedance shift, or a shift in temperature. When exposed to the explosive material 16 or other target chemical species 12, the cantilevered probes 30 also may increase or decrease in mass, or become more or less rigid. These and other responses may result in the generation of a piezoelectric element output signal.

In one example, the cantilevered probe 30 comprises a patterned layer of gold. When exposed to mercury, the gold and mercury react to form an amalgam. The gold-mercury amalgam adds mass to the cantilevered probe 30 and therefore tends to decrease the resonant frequency of the cantilevered probe 30. Amalgam formation, however, also increases the mechanical stiffness of the cantilevered probe 30, thereby increasing its natural resonant frequency. These two effects tend to cancel each other, though one effect can be made dominant by careful selection and placement of a chemical-sensitive selective coating 34 on the cantilevered probe 30.

In one exemplary detection mode, the adsorbed explosive material 16 deflagrates or ignites when heated by a probe heater 36 to cause an exothermic reaction, which in turn causes a piezoelectric output signal to be generated by a piezoelectric element 32. For example, the piezoelectric element 32 may generate an electrical charge when the probe heater 36 heats the cantilevered probe 30. The piezoelectric element 32 also may detect an increase in temperature of the cantilevered probe 30 when the exothermic reaction occurs. Alternatively, the explosive material 16 may melt or evaporate when the probe heater 36 heats the cantilevered probe 30 and the phase transformation may be detected with the piezoelectric element 32. Alternatively, the explosive material 16 may be detected by an impedance shift of the piezoelectric element 32 when the probe heater 36 heats the cantilevered probe 30. The reactive portion, the resistive portion or a combination of both may shift in response to heating of the cantilevered probe 30.

In some embodiments, the piezoelectric characteristics of the piezoelectric element 32 may detect a shift in bending of the cantilevered probe 30 as the explosive material 16 is adsorbed onto a surface of the cantilevered probe 30, is desorbed from the cantilevered probe 30, or reacts exothermically on the cantilevered probe 30. For example, as the explosive material 16 accumulates on the cantilevered probe 30, the cantilevered probe 30 may bend upwards or downwards depending on the stress state of the added or removed material. Alternatively or in conjunction, the piezoelectric element 32 may detect a shift in a resonant frequency of the cantilevered probe 30 when the explosive material 16 is adsorbed onto the cantilevered probe 30, is desorbed from the cantilevered probe 30, or reacts exothermally on the cantilevered probe 30. For example, as the explosive material 16 accumulates on the cantilevered probe 30, the resonant frequency may decrease due to the additional mass loading. Similarly, as the explosive material 16 desorbs or is otherwise removed, the resonant frequency may return towards its previous condition prior to mass loading. The effects described above may occur in various combinations. Analysis of one or a multiplicity of these effects may be used to identify an explosive or a non-explosive material absorbed onto cantilevered probe 30.

The probe heater 36, a piezoresistor serving as a temperature sensor, the piezoelectric element 32, or another on-board temperature sensor may be used to indicate the temperature of the cantilevered probe 30, from which the ignition temperature or deflagration temperature of the explosive material 16 may be determined. Alternatively, an onboard temperature sensor may be used to determine the heat of vaporization, melting temperature, phase change, chemical reactions, exothermic reactions, endothermic reactions, or time dependencies thereof associated with the explosive material 16 or other target chemical species 12 to aid in the identification.

As discussed above, one or more selective coatings 34 may be disposed on one or more cantilevered probes 30 in the cantilevered probe array 20 to facilitate chemical detection and specificity. For example, one or more cantilevered probes 30 in the cantilevered probe array 20 may be coated, uncoated, or otherwise treated to detect the explosive material 16. The selective coating 34 may be applied to a portion of one or more of the cantilevered probes 30 in the cantilevered probe array 20. For example, the selective coating 34 may be applied to the topside or bottom side of one or more of the cantilevered probes 30 or to portions thereof. The selective coating 34 can include, for example, an epoxy resin such as Novolac™, a fluoropolymer such as FluoroPel™, a gold layer, a palladium layer, an alcohol-absorbent polymer, a water-absorbent material, a chemical-sensitive polymer, a chemical-sensitive layer, a biosensitive material, a thiol, or derivatives or combinations thereof.

Various application methods can be used to deposit or apply the selective coating 34 and to otherwise treat surfaces of the cantilevered probes 30. The selective coatings 34 can comprise, for example, a dipped coating, a sprayed coating, or a dispensed coating disposed on at least a portion of one or more of the cantilevered probes 30. An exemplary chemical-sensitive selective coating 34 includes a masked coating disposed on a portion of one or more of the cantilevered probes 30. In an alternative application method, a non-homogeneous coating material is applied to a set of cantilevered probes 30 in the cantilevered probe array 20, such that constituents of the non-homogeneous coating material are deposited on the cantilevered probes 30 with suitable variations in composition, coverage, and/or thickness.

In some disclosed embodiments, the chemical detection system 10 includes one or more reference cantilevered probes 30$r$ in the cantilevered probe array 20. The reference cantilevered probe 30$r$ can provide a reference cantilevered probe response when the cantilevered probe array 20 is exposed to the explosive material 16 or other target chemical species 12. The reference cantilevered probes 30$r$ can be formed, for example, with no coating materials disposed thereon to reduce or eliminate sensitivity to the explosive material 16 or other target chemical species 12. Alternatively, the reference cantilevered probes 30$r$ can have an inert coating disposed on their surface to reduce or eliminate sensitivity to the explosive material 16. Alternatively, one or more reference cantilevered probes 30$r$ can be mechanically isolated from exposure to the explosive material 16 while other portions of the cantilevered probe array 20 are exposed.

The explosive material 16, which may be located in a liquid or gas carrier 14, such as air, water, low-pressure gas, or plasma, can be transported in a forced or free manner towards the cantilevered probes 30. Once the explosive material 16 makes contact with surfaces of the cantilevered probes 30 it may invoke, for example, shifts in resonant frequency, Q factor, impedance, phase, or deflection amplitudes. Impedance shifts may be obtained, for example, by absorbing explosive material 16 or other target chemical species 12 directly into the bulk of a piezoelectric or pyroelectric film of the piezoelectric element 32. The absorption may be enhanced, for example, by increasing the periphery of unpassivated sidewalls, such as with narrow line widths and small spaces between multiple segments of the piezoelectric element 32.

The cantilevered probe array 20 may be actuated with an excitation voltage applied to a piezoelectric drive mechanism serving optionally as the piezoelectric element 32 disposed on each of the cantilevered probes 30 in the cantilevered probe array 20. To reduce the number of external pads and connections, a group of cantilevered probes 30 may be connected in series and electrically connected to a pair of cantilevered probe array drive pads 24, which may be electrically connected to an interface circuit 40. While this configuration can increase the series resistance of the string, differentiation of individual cantilevered probes 30 may be made by detection of signals at or near the resonant frequency of the selected cantilevered probes 30. Alternatively, a group of cantilevered probes 30 may be connected in parallel and electrically connected to a pair of cantilevered probe array drive pads 24, increasing the effective capacitance and decreasing the effective resistance, while still allowing differentiation of individual cantilevered probe responses based on frequency. Alternatively, cantilevered probes 30 may be connected in a network of series-connected and parallel-connected cantilevered probes with frequency-identifiable addressable elements.

The interface circuit 40 can provide excitation voltages for piezoelectric material on the cantilevered probes 30 and sense deflections and vibrations of the cantilevered probes 30 with the same or a different piezoelectric material. In one example, the interface circuit 40 includes an adjustable frequency generator that is scanned through a predetermined frequency range to excite one or more of the cantilevered probes 30 in the cantilevered probe array 20. In another example, the interface circuit 40 includes an impedance analyzer that is scanned through a resonant frequency of at least one cantilevered probe 30, measuring the magnitude and phase from the cantilevered probes 30 and monitoring for any variations in impedance as the cantilevered probes 30 are exposed to one or more explosive materials 16. In another example, the interface circuit 40 includes an oscillator circuit operating at a resonant frequency of at least one cantilevered probe 30 in the cantilevered probe array 20.

In another example, the interface circuit 40 includes an oscillator circuit operating at a predetermined frequency that is near, yet off-resonance with respect to one or more of the cantilevered probes 30 in the cantilevered probe array 20. This configuration may result in the generation of higher amplitudes of vibration and therefore higher output signals as the resonant frequency of the selected cantilevered probe 30 shifts and moves towards the predetermined frequency. The predetermined frequency may be set, for example, slightly above or slightly below the resonant frequency of one or more of cantilevered probes 30.

In another example, the amplitude of bending and/or vibration is monitored as the cantilevered probe 30 strikes against a fixed or adjustable mechanical stop such as a piezoelectric slab or a piezotube. In another example, the interface circuit 40 includes an impulse circuit for applying an electrical impulse to the cantilevered probe array 20, and the ring-down of the cantilevered probes 30 is monitored. In another example, noise, such as pink noise or white noise, is applied to excite the cantilevered probe array 20. In some embodiments, the interface circuit 40 includes a network analyzer for detecting signals from the cantilevered probe array 20. The interface circuit 40 or a controller 50 may include a fast Fourier transform generator to perform a fast Fourier transform (FFT) on the shifted cantilevered probe response, and to provide respective frequencies of the cantilevered probes 30 in the cantilevered probe array 20, which can be correlated with previously measured probe responses and used to identify the explosive material 16 and/or other target chemical species 12.

As discussed above, the chemical detection system 10 may include an interface circuit 40 electrically coupled to a piezoelectric element 32 that enables the detection of an explosive material 16 and/or a target chemical species 12. The interface circuit 40 may contain, for example, the piezoelectric element 32 as a bridge element in an AC bridge circuit. The AC bridge circuit may be tuned to an on-resonance condition or on off-resonance condition to detect the explosive material 16. In operation, the output of the AC bridge circuit may shift as the resonant frequency of the cantilevered probe 30 moves off-resonance with the addition or subtraction of mass. Alternatively, the output of the AC bridge circuit may shift as the resonant frequency of the cantilevered probe 30 moves towards the off-resonance tuned condition. Off-resonance tuning can allow any signals generated by the piezoelectric element 32 to be distinguished from any output due to vibrations of the cantilevered probe 30. In some embodiments, one or more of the cantilevered probes 30 in the cantilevered probe array 20 are tuned to an on-resonance condition, and one or more other cantilevered probes 30 in the cantilevered probe array 20 are tuned to an off-resonance condition to detect the explosive material 16.

The interface circuit 40 may detect shifted cantilevered probe responses from one or more actuated cantilevered probes 30 in the cantilevered probe array 20. Examples of shifted cantilevered probe responses include a shift in a resonant frequency of one or more of the cantilevered probes 30, a shift in a quality (Q) factor of one or more of the cantilevered probes 30, a shift in impedance of one or more of the cantilevered probes 30, a shift in phase of one or more of the cantilevered probes 30, a shift in deflection amplitude of one or more of the cantilevered probes 30, and combinations thereof. With exposure to the explosive material 16 or other target chemical species 12, one or more cantilevered probes 30 in the cantilevered probe array 20 can exhibit shifts in various properties. Similarly, with exposure to more than one explosive material 16 or other target chemical species 12, one or more cantilevered probes 30 in the cantilevered probe array 20 may exhibit shifts from which multiple explosive materials 16 and/or other target chemical species 12 can be determined.

A controller 50 such as a central processing unit (CPU), a digital signal processor (DSP), a microcontroller, or a field-programmable gate array (FPGA) may be included in the chemical detection system 10 to execute programmed code and provide monitoring, controlling and analyzing functions. The controller 50 can be in electrical communication with the interface circuit 40 and may be located, for example, on a substrate 22 along with the cantilevered probe array 20, within an enclosure 60 on the same circuit board or in the same package as the cantilevered probe array 20, or located remotely with respect to the enclosure 60. The controller 50 may internally contain the functions and capabilities of the interface circuit 40. The controller 50 may receive shifted cantilevered probe responses from a set of one or more of the cantilevered probes 30 in the cantilevered probe array 20.

The explosive material 16 and other target chemical species 12 may be determined based on the shifted cantilevered probe response using, for example, an algebraic model that relates shifts in cantilevered probe responses to explosive materials and concentration. Alternatively, the explosive material 16 may be determined based on a comparison between the shifted cantilevered probe responses and a reference set of cantilevered probe responses. Such reference sets can be obtained by exposing the cantilevered probes 30 to controlled environments with known explosive materials and concentrations during calibration at the factory or on site. The controller 50 can determine one or more explosive material 16, for example, through pattern recognition techniques, statistical processes, or fuzzy logic with comparison to the reference set of cantilevered probe responses. The reference set of cantilevered probe responses can comprise, for example, a learned set obtained from shifts in cantilevered probe responses by cantilevered probes 30 that have been exposed to known explosive materials and concentrations under controlled laboratory or factory environments.

In some embodiments, heating of select cantilevered probes 30 burns off, evaporates off, or otherwise cleans and resets the cantilevered probe 30 to a nascent condition. In these and other embodiments, the probe heater 36 may be coupled to at least one cantilevered probe 30 in the cantilevered probe array 20. The probe heater 36 may be formed, for example, with a resistive layer disposed on the surface of or formed within the cantilevered probe 30, such as by ion implantation. Exemplary probe heaters 36, which may be connected in series or parallel or individually connected, can be formed on one, several, or all of the cantilevered probes 30 within the cantilevered probe array 20. The probe heaters 36 also may be used to react the explosive material 16 on the cantilevered probe 30 by heating the probe to a predetermined temperature where the reaction can occur. Alternatively, the probe heaters 36 may be used to ignite or deflagrate condensate of explosive vapors on the cantilevered probes 30. The probe heater 36 can comprise, for example, a resistive or a piezoresistive element formed in one or more of the cantilevered probes 30 or a heater element, such as a patterned metal film, disposed on a surface of the cantilevered probe 30.

The piezoelectric element 32, which may also serve as a piezoelectric drive mechanism, can comprise, for example, zinc oxide, lead zircanate titanate, aluminum nitride, a piezoelectric material, or derivatives or combinations thereof. The piezoelectric element 32 also can comprise a pyroelectric material. Piezoelectric materials typically expand or contract when driving voltages are applied, and conversely generate a voltage when stressed or compressed. Piezoelectric materials are generally pyroelectric, in that a pyroelectric charge, voltage or current is generated when the material is heated. For example, the piezoelectric element 32 may generate a piezoelectric element output signal when the explosive material 16 in proximity to the piezoelectric element 32 ignites, deflagrates or otherwise generates heat. In some embodiments, the piezoelectric element 32 serves simultaneously as a piezoelectric thermal detector and a piezoelectric drive mechanism to drive and excite the cantilevered probe 30, such as into resonance. In other embodiments, the piezoelectric element 32 is separated from a piezoelectric drive mechanism, such as a piezoelectric drive mechanism that also is located on a surface of cantilevered probe 30.

The chemical detection system 10 may contain one or more cantilevered probe arrays 20 in an enclosure 60, which may include an inlet port 62 and an outlet port 64 for transport of the explosive material 16, the target chemical species 12, and the carrier 14. The explosive material 16 may enter the enclosure 60 through the inlet port 62 and be exposed to the cantilevered probe array 20. The explosive material 16 or byproducts thereof may exit through the outlet port 64. The enclosure 60 also may include filters, scrubbers, and other media treatment elements to aid in the detection of the explosive material 16.

A transport mechanism 66 such as a pump or a fan with ductwork or piping may be included for transporting the explosive material 16 to the cantilevered probe array 20. The chemical detection system 10 also may include an explosive material concentrator 68 coupled to one or more of the cantilevered probes 30. The concentrator 68, such as a pressurizing system or a condenser and heater system, may be included to concentrate the explosive material 16 and/or other target chemical species 12 proximal to the cantilevered probe array 20 to facilitate detection. In some embodiments, the explosive material 16 is concentrated on one or more cantilevered probes 30 when the concentrator 68 is locally heated.

The chemical detection system 10 may include a thermally conductive mesh 58 such as a copper screen or a metal mesh substantially surrounding the cantilevered probes 30 to limit the egression of thermal energy, such as from an exothermic reaction. As the explosive material 16 deflagrates, ignites or otherwise burns, hot air may be generated near the cantilevered probe 30. The thermally conductive mesh 58 may facilitate cooling of the hot air and otherwise limit heat transfer away from the cantilevered probes 30, such as beyond the enclosure 60.

The chemical detection system 10 may be connected to a local area network (LAN), a wide area network (WAN), the Internet, or other networked communication system via one or more wired or wireless connections. The chemical detection system 10 may be installed, for example, into an air handling system of a building or airport that has many inlets, into a standalone unit with a portal for chemical detection, or into a handheld unit for portable use. Moreover, the chemical detection system 10 may be installed in shipping containers and crates during storage and transit for chemical detection and monitoring.

Figure 2:
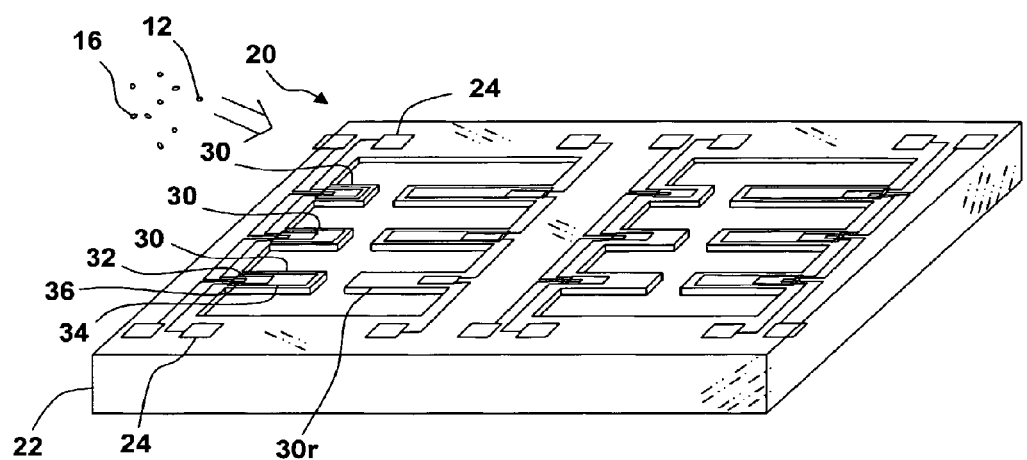
FIG. 2 is a perspective view of a self-sensed cantilevered probe array, in accordance with some embodiments of the current invention.

FIG. 2 illustrates a self-sensed cantilevered probe array, in accordance with some embodiments of the present invention. As shown, the self-sensed cantilevered probe array 20 includes a plurality of cantilevered probes 30 on a substrate 22. The cantilevered probes 30 can include piezoelectric elements 32, probe heaters 36, and/or chemical-sensitive selective coatings 34. Variations in length or thickness of the cantilevered probes 30 and variations in the thickness and coverage of the applied coatings may allow for frequency differentiation between the cantilevered probes 30 within the cantilevered probe array 20.

The cantilevered probes 30 may have a rectangular shape, though other shapes may be suitably used, such as pointed cantilevers, V-shaped cantilevers, triangular-shaped cantilevers, dual-arm cantilevers, or balanced cantilevers. The cantilevered probes 30 may be arranged and attached to the substrate 22 in an array in which the cantilevered probes are all identical, all different, or combinations thereof.

In some embodiments, the cantilevered probe array 20 is actuated with an excitation voltage applied to a piezoelectric element 32 that serves as a piezoelectric drive mechanism and as a piezoelectric sense mechanism. In one example, the cantilevered probes 30 are series-connected to a pair of cantilevered probe array drive pads 24 on the substrate 22. The cantilevered probes 30 also can be parallel connected to the pair of cantilevered probe array drive pads 24. The cantilevered probe array 20 also can comprise a network of series-connected and parallel-connected cantilevered probes that connect electrically to the pair of cantilevered probe array drive pads 24. More than one group or array of cantilevered probes 30 may be included on the substrate 22. Additional connections with associated pads may be made to the piezoelectric elements 32 on particular cantilevered probes 30. The substrate 22 also may have through-wafer vias for backside connection to the drive pads 24.

The substrate 22 can include a semiconductor substrate such as a silicon wafer, a silicon-on-insulator (SOI) wafer, a glass substrate, or other suitable substrate for forming the cantilevered probes 30 thereon. The cantilevered probes 30 can comprise materials such as silicon, polysilicon, silicon nitride, zinc oxide, aluminum nitride, metals, pyroelectric materials, piezoelectric materials, or derivatives or combinations thereof. These materials can be present in various forms, such as sheets, films and layers. For example, a zinc oxide, PZT or aluminum nitride film can be deposited on a layer of single-crystal silicon, patterned, and etched. Conductive layers for top and bottom electrodes, interconnections, and probe heater connections then can be deposited and etched accordingly. The cantilevered probes 30 can be defined with a photomask and associated lithographic sequences along with deep reactive ion etching (D-RIE) or anisotropic etching of the cantilevers and substrate. This allows the formation and freeing of the silicon cantilevers with interconnected ZnO electrodes in series, parallel, or series-parallel configurations. Excitation and detection of the cantilevers can occur with voltages applied to the piezoelectric material. The piezoelectric elements 32 may be formed with deposition and patterning processes as are known in the art. The probe heaters 36 on the cantilevered probes 30 can be formed, for example, by selectively implanting portions of the cantilevered probe 30 or by depositing, patterning and etching a metal film on the cantilevered probe 30.

A chemical-sensitive selective coating 34 may be applied to at least a portion of one or more of the cantilevered probes 30. The chemical-sensitive coating 34 can include a material, such as an epoxy resin, a fluoropolymer, gold, palladium, an alcohol-absorbent polymer, a water-absorbent material, a chemical-sensitive polymer, a chemical-sensitive material, a biosensitive material, a thiol, or derivatives or combinations thereof. The chemical-sensitive selective coating 34 may be applied, for example, with techniques such as dipping, spraying, or dispensing the coating on at least a portion of one or more of the cantilevered probes 30. The chemical-sensitive coating material may be applied onto a portion of one or more of the cantilevered probes 30 with the use of stencil masks or photomasks and photolithographic patterning techniques. The chemical-sensitive selective coating 34 may be applied in conjunction with photolithographic patterning, for example, using standard sputtering and other deposition techniques known in the art.

Multiple masking sequences can be used to apply multiple coating materials. Alternatively, multiple-component chemical-sensitive selective coatings 34 may be used. The multiple-component chemical-sensitive selective coatings 34 can comprise, for example, non-homogeneous coating materials, which can be applied in such a way that variations in coating thickness and/or composition occur when the materials are deposited.

When exposed to the explosive material 16 or to the target chemical species 12, one or more of the cantilevered probes 30 in the cantilevered probe array 20 may undergo an electrical or a mechanical shift, such as a shifted resonant frequency, a shifted Q factor, a shifted impedance, a shifted phase, or a shifted deflection amplitude. The cantilevered probe array 20 may include one or more reference cantilevered probes 30r to provide a reference cantilevered probe response when the cantilevered probe array 20 is exposed to the explosive material 16 or to the target chemical species 12. The reference cantilevered probes 30r may be uncoated, coated with an inert material, or otherwise protected from exposure to the explosive material 16 and the target chemical species 12.

Figure 3:
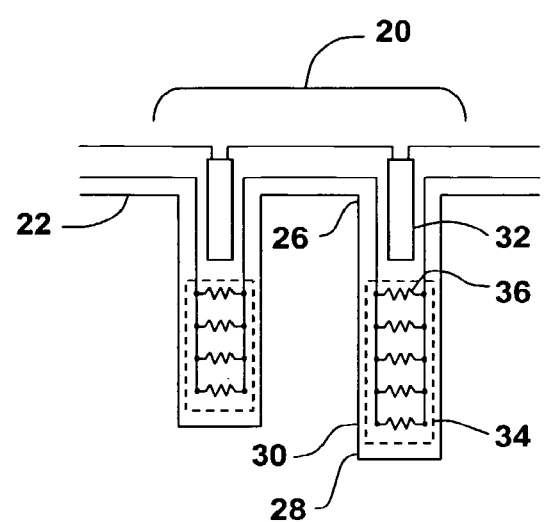
FIG. 3 is a plan view of a pair of cantilevered probes with probe heaters and piezoelectric detectors, in accordance with some embodiments of the current invention.

FIG. 3 is a plan view of a pair of cantilevered probes 30 with probe heaters 36 and piezoelectric elements 32 for detecting an explosive material, in accordance with some embodiments of the present invention. As shown, one or more probe heaters 36 are disposed on or formed in the cantilevered probes 30. The probe heater 36 heats the cantilevered probes 30, for example, to initialize the cantilevered probes 30 prior to exposing the cantilevered probe array 20 to the explosive material. The probe heaters 36 also can be used to burn off, deflagrate, or otherwise react an explosive material that is adsorbed onto a surface of the cantilevered probe 30.

The piezoelectric elements 32, which may also serve as piezoelectric drive mechanisms for the cantilevered probes 30, can be configured to detect an explosive material adsorbed onto the cantilevered probe 30 when the cantilevered probe 30 is heated by the probe heater 36 to cause, for example, an exothermic reaction. In one example, the piezoelectric element 32 generates a piezoelectric element output signal when the probe heater 36 heats the adsorbed explosive material and an exothermic reaction or a phase change occurs. In another example, the piezoelectric element 32 detects an increase in temperature of the cantilevered probe 30 when an exothermic reaction occurs. In another example, the piezoelectric element 32 detects a shift in bending of the cantilevered probe 30 when the explosive material is adsorbed onto the cantilevered probe 30, is desorbed from the cantilevered probe 30, or reacts exothermically on the cantilevered probe 30. In another example, the piezoelectric element 32 detects a shift in a resonant frequency of the cantilevered probe 30 when the explosive material is adsorbed, is desorbed or exothermically reacts. In another example, the piezoelectric element 32 detects an impedance shift when the explosive or non-explosive material is adsorbed, is desorbed or exothermically reacts.

As show in FIG. 3, the cantilevered probe 30 can include a base end 26 and a tip 28. The cantilevered probe array 20 may be attached to a common base such as a substrate 22. The cantilevered probe 30 may have a rectangular shape, although other shapes may be suitably used, such as pointed shapes, V-shapes, triangular-shapes, or dual-arm shapes. A treated portion, such as the selective coating 34 disposed on at least a portion of the cantilevered probe 30, may aid in discriminating between various explosive materials and other target chemical species 12. In some embodiments, the cantilevered probe 30 is attached at each end, with the center of the cantilevered probe 30 free to vibrate. In another embodiment, the cantilevered probe 30 is attached on all sides in a diaphragm or membrane configuration.

A drive mechanism, such as the piezoelectric element 32 serving as a piezoelectric drive mechanism or a separate piezoelectric drive element, can be coupled to the cantilevered probe 30. The piezoelectric element 32 and/or the drive mechanism may comprise, for example, a patterned thin film of zinc oxide, PZT or aluminum nitride on a surface of the cantilevered probe 30. A sense mechanism may also be coupled to the cantilevered probe 30. The sense mechanism may comprise, for example, a piezoresistor attached to or formed in the cantilevered probe 30.

The probe heater 36 can be coupled to the cantilevered probe 30. The probe heater 36 can comprise, for example, a probe heater formed in or on the cantilevered probe 30. In addition to initiating an exothermic reaction or a phase change, the probe heater 36 may be used to heat the cantilevered probe 30 to an elevated temperature that initializes or re-initializes the treated portion or the selective coating 34. Alternatively, an external probe heater such as a heat lamp or a hot gas system may be used to heat and re-initialize the cantilevered probe 30. Chemical re-initialization may be accomplished, for example, by using cleaning processes or by reversing any chemical reactions that occurred on the treated portion.

Multiple cantilevered probes 30 may be arranged in a cantilevered probe array 20, the cantilevers being all identical, all different, or some combination thereof. The cantilevered probes 30 of a cantilevered probe array 20 may be driven and sensed, for example, with a piezoelectric drive element coupled to each cantilevered probe 30. In one embodiment, the piezoelectric elements in the array are connected in series. The series-connected piezoelectric elements in the array may be driven with as few as two electrical connections to the piezoelectric element array. Scanning the drive voltage through a range of frequencies can excite and sense one cantilevered probe 30 at a time, allowing interrogation of any cantilevered probe 30 in the array while minimizing the number of electrical connections required. In another configuration, the piezoelectric elements in the array are connected in parallel, such that as few as two electrical connections may be used to drive and sense cantilevered probes 30. In this configuration, failure of one cantilevered probe 30 does not prevent others from operating. In another configuration, the array of piezoelectric elements is connected in a series-parallel arrangement.

Figure 4:
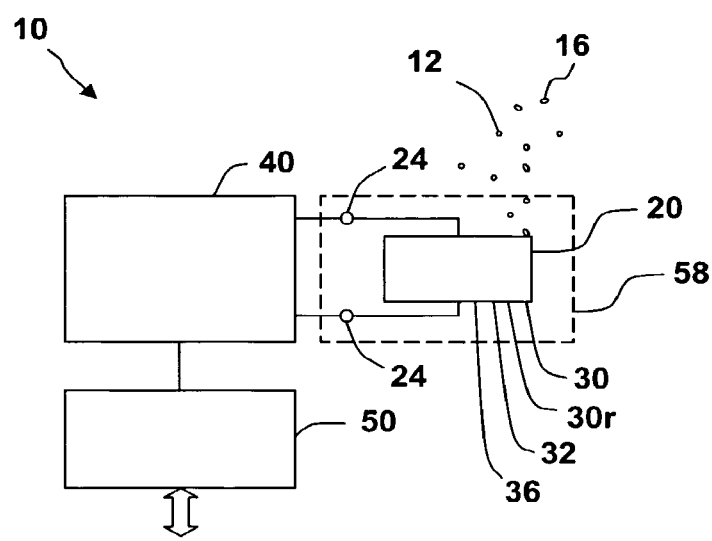
FIG. 4 is a schematic diagram of a system for detecting an explosive material, in accordance with some embodiments of the current invention.

FIG. 4 is a schematic diagram of a system for detecting an explosive material, in accordance with some embodiments of the present invention. As shown, the chemical detection system 10 includes one or more cantilevered probes 30, one or more probe heaters 36 thermally coupled to the cantilevered probes 30, and one or more piezoelectric elements 32 disposed on the cantilevered probes 30. A controller 50 and an interface circuit 40 may be connected to one or more of the self-sensed cantilevered probes 30 configured in the self-sensed cantilevered probe array 20. The controller 50, which can be connected to the interface circuit 40, can be configured to drive and sense a plurality of self-sensed cantilevered probes 30 in the cantilevered probe array 20. It should be observed that, in some embodiments, the cantilevered probe array 20 may be electrically connected to the interface circuit 40 with as few as two cantilevered probe array drive pads 24. At least one cantilevered probe 30 in the cantilevered probe array 20 may exhibit a shifted cantilevered probe response when the cantilevered probe array 20 is exposed to an explosive material 16 or a target chemical species 12 and the cantilevered probe array 20 is actuated by the interface circuit 40. The piezoelectric element 32 can generate a piezoelectric element output signal that may be analyzed by the controller 50.

The interface circuit 40 can be configured to actuate the cantilevered probe array 20 with an excitation voltage applied to a piezoelectric material such as piezoelectric element 32 disposed on each cantilevered probe 30 in the cantilevered probe array 20. In one example, the interface circuit 40 includes an adjustable frequency generator that is scanned through a predetermined frequency range. In another example, the interface circuit 40 includes an impedance analyzer that is scanned through a resonant frequency of one or more cantilevered probes 30 in the cantilevered probe array 20. In another example, the interface circuit 40 includes an oscillator circuit operating at a resonant frequency of at least one cantilevered probe 30 in the cantilevered probe array 20. In another example, the interface circuit 40 includes an oscillator circuit operating at a predetermined frequency that is set to be off-resonance with respect to at least one cantilevered probe 30 in the cantilevered probe array 20. In another example, the interface circuit 40 includes control circuitry to monitor the amplitude of bending and vibration as the cantilevered probe 30 strikes against a fixed or adjustable mechanical stop. In another example, the interface circuit 40 comprises an impulse circuit for applying an electrical impulse to all of the cantilevered probes 30 in the cantilevered probe array 20. In another example, the interface circuit 40 or the controller 50 includes a fast Fourier transform (FFT) generator to perform a fast Fourier transform on the shifted cantilevered probe response. The interface circuit 40 can be configured to detect a shifted cantilevered probe response from one or more actuated cantilevered probes 30, such as a shifted resonant frequency, a shifted Q factor, a shifted impedance, a shifted phase, or a shifted deflection amplitude.

The controller 50 may receive a shifted cantilevered probe response from a set of one or more cantilevered probes 30 in the cantilevered probe array 20. The explosive material 16 or other target chemical species 12 may be determined, for example, based on the shifted cantilevered probe response. For example, the explosive material 16 may be determined based on a comparison between the shifted cantilevered probe response and a reference set of cantilevered probe responses. The reference set of cantilevered probe responses can comprise, for example, a learned set obtained during the calibration of the chemical-sensing system or from a statistical database of cantilevered probe responses.

To cancel out common mode effects such as temperature, one cantilevered probe 30 in the cantilevered probe array 20 may be a reference cantilevered probe 30r, wherein the reference cantilevered probe 30r provides a reference cantilevered probe response when the cantilevered probe array 20 is exposed to the explosive material 16 or the target chemical species 12.

In some embodiments, the explosive material 16 and/or other target chemical species 12 are adsorbed onto the cantilevered probe 30 by exposing the cantilevered probe 30 to an environment containing the explosive material 16 and/or the other target chemical species 12. To increase the rate of adsorption, transport mechanisms and concentrators may be added to the chemical detection system 10.

Using heat generated by the onboard probe heater 36 or an external probe heater thermally coupled to the cantilevered probe 30, the adsorbed explosive material 16 may ignite, deflagrate or otherwise burn. The chemical detection system 10 may include a thermally conductive mesh 58 substantially surrounding the cantilevered probes 30 to limit the egression of thermal energy from an exothermic reaction. A piezoelectric element 32 disposed on the cantilevered probe 30 can generate, for example, a piezoelectric element output signal when an exothermic reaction occurs. Alternatively or in addition, the piezoelectric element 32 may also serve as a piezoelectric drive mechanism and a piezoelectric sense mechanism that senses the explosive material 16 by detecting bending or shifts in a resonant frequency of the cantilevered probe 30.

Detection of a non-explosive material or other target chemical species 12 adsorbed onto a surface of the cantilevered probe 30 may be accomplished, for example, using characteristic bending shifts, frequency shifts, exothermic or non-exothermic reaction indicators, phase change indicators, impedance shifts, or a combination thereof. Specificity and delineation of the explosive material 16 and other target chemical species 12 may be increased with selective coatings applied to one or more of the cantilevered probes 30 in the cantilevered probe array 20.

Figure 5A:
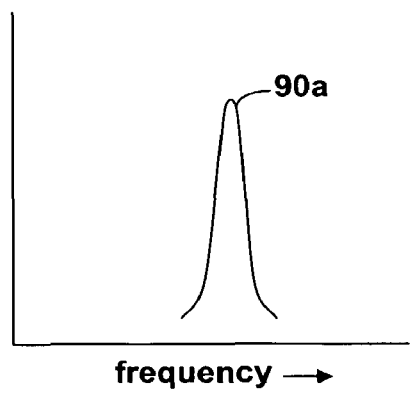
FIG. 5a, FIG. 5b and FIG. 5c are graphs showing characteristic resonant frequencies of a cantilevered probe prior to exposure to an explosive material, after exposure to the explosive material, and after deflagration or ignition of the explosive material, respectively, in accordance with some embodiments of the current invention.
Figure 5B:
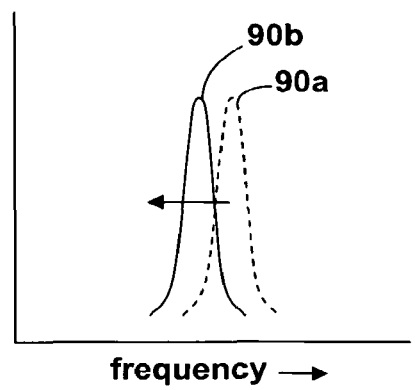
Figure 5C:
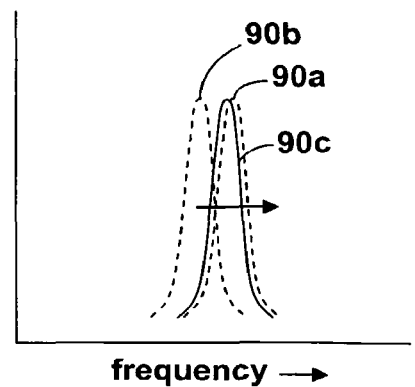

FIG. 5a, FIG. 5b and FIG. 5c show characteristic resonant frequencies of a cantilevered probe prior to exposure to an explosive material, after exposure to the explosive material, and after deflagration, ignition, or evaporation of the explosive material, respectively, in accordance with some embodiments of the present invention. An exemplary response of a cantilevered probe with resonant frequency 90a is seen in FIG. 5a. As the explosive material is adsorbed onto the cantilevered probe, the resonant frequency decreases with mass loading indicated by shifted resonant frequency 90b, as seen in FIG. 5b. After the explosive material deflagrates, ignites, or otherwise desorbs from the cantilevered probe, the response curve with resonant frequency 90c returns towards the resonant frequency 90a, as seen in FIG. 5c. Time dependencies of the frequency shifts prior to, during, or after cantilevered probe heating may provide characteristics associated with various absorbed and desorbed explosive and non-explosive materials. Frequency shifts with the application of predetermined cantilever heating profiles may also provide characteristic signatures for the adsorbed materials.

Figure 6A:
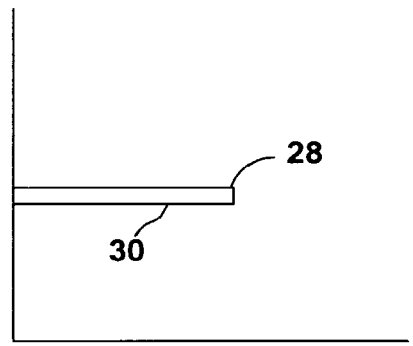
FIG. 6a, FIG. 6b and FIG. 6c are elevation views showing characteristic bending of a cantilevered probe prior to exposure to an explosive material, after exposure to the explosive material, and after deflagration or ignition of the explosive material, respectively, in accordance with some embodiments of the current invention.
Figure 6B:
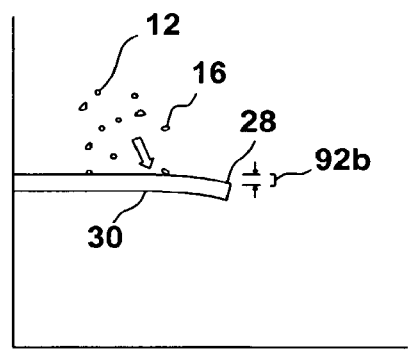
Figure 6C:
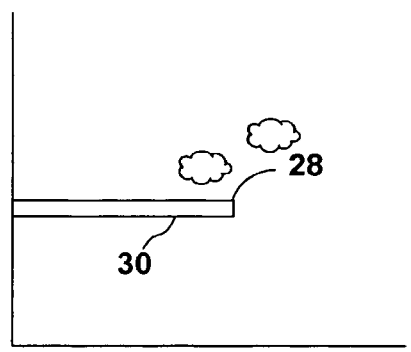

FIG. 6a, FIG. 6b and FIG. 6c show characteristic bending of a cantilevered probe prior to exposure to an explosive material, after exposure to the explosive material, and after deflagration or ignition of the explosive material, respectively, in accordance with some embodiments of the present invention. In some embodiments, the cantilevered probe 30 initially has a tip 28 that is essentially straight, as seen in FIG. 6a. With exposure to and adsorption of the explosive material 16 or other target chemical species 12 onto a surface of the cantilevered probe 30, the probe may remain neutral, bend upwards, or bend downwards depending on the stress state of the cantilevered probe 30, with the tip 28 deflecting an amount equal to a displacement 92b, as seen in FIG. 6b. When the cantilevered probe 30 is heated with an onboard or external probe heater, the explosive material 16 may deflagrate, ignite, or otherwise desorb from the surface of the cantilevered probe 30, allowing the cantilevered probe 30 to return towards the initial, undeflected state with the tip 28 back in a neutral position, as seen in FIG. 6c. It should be noted that localized heating of the cantilevered probe 30 may contribute to beam bending, as thermal gradients across the cantilever produce moments that can cause bending.

Figure 7A:
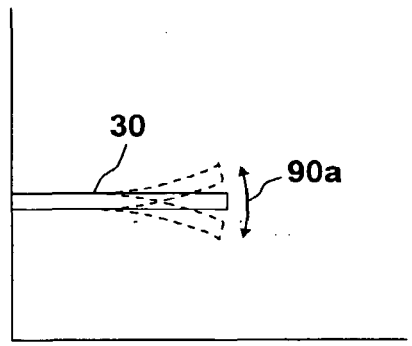
FIG. 7a, FIG. 7b and FIG. 7c are elevation views showing bending and vibrations of a cantilevered probe prior to exposure to an explosive material, after exposure to the explosive material, and after deflagration or ignition of the explosive material, respectively, in accordance with some embodiments of the current invention.
Figure 7B:
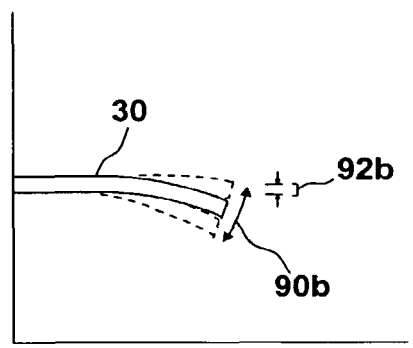
Figure 7C:
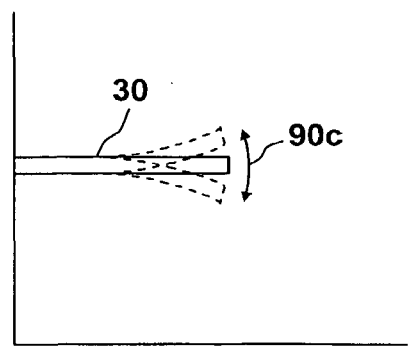

FIG. 7a, FIG. 7b and FIG. 7c illustrate simultaneous bending and vibration of a cantilevered probe prior to exposure to an explosive material, after exposure to the explosive material, and after deflagration or ignition of the explosive material, respectively, in accordance with some embodiments of the present invention. The cantilevered probe 30 vibrates at resonant frequency 90a about a neutral position prior to mass loading, as seen in FIG. 7a. With the addition of explosive material on the cantilevered probe 30, the tip may deflect an average amount equal to a displacement 92b while vibrating at a shifted or unshifted resonant frequency 90b, as seen in FIG. 7b. After deflagration, ignition, or desorption of the explosive material from the cantilevered probe 30, the tip may return towards the initial, undeflected state while vibrating at a resonant frequency 90c, as seen in FIG. 7c.

Figure 8A:
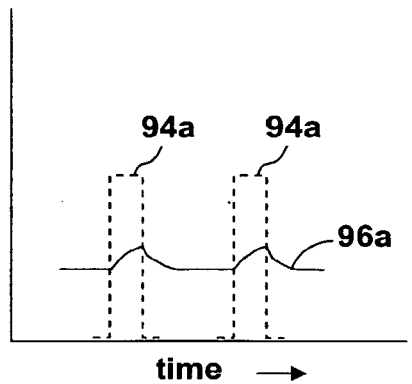
FIG. 8a, FIG. 8b and FIG. 8c are graphs showing periodic heating of a cantilevered probe prior to exposure to an explosive material, during exposure to the explosive material, and after deflagration or ignition of the explosive material, respectively, along with a generated piezoelectric detector output signal, in accordance with some embodiments of the current invention.
Figure 8B:
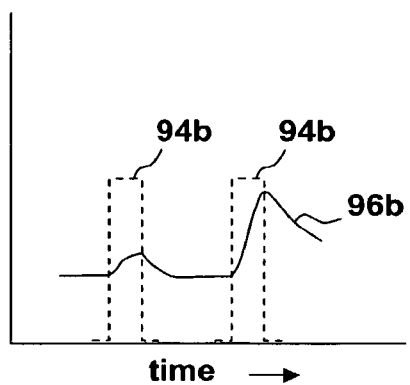
Figure 8C:
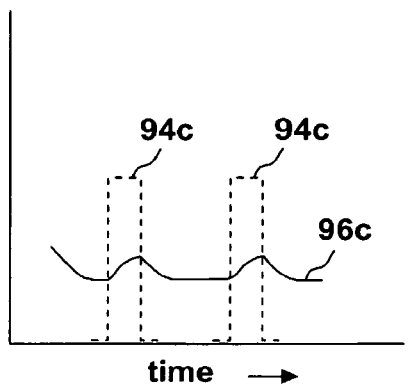

FIG. 8a, FIG. 8b and FIG. 8c illustrate periodic heating of a cantilevered probe prior to exposure to an explosive material, during exposure to the explosive material, and after deflagration or ignition of the explosive material, respectively, along with a generated piezoelectric element output signal, in accordance with some embodiments of the present invention. A piezoelectric element may generate a relatively small peak during each periodic heating cycle 94a of the cantilevered probe and return to a low level as the cantilevered probe cools, as indicated by the piezoelectric element output signal 96a in FIG. 8a. As the explosive material deposits and is adsorbed onto the cantilevered probe, the piezoelectric element output signal 96a replicates relatively small peaks during each periodic heating cycle 94b, until sufficient explosive material is adsorbed so that the explosive material deflagrates and ignites or otherwise combusts, thereby generating a high-level piezoelectric element output signal 96b corresponding to the energy released by the exothermic reaction, as seen in FIG. 8b. Other mechanisms such as melting or evaporation may provide piezoelectric element output signals 96b with higher, lower, or time-dependent characteristics different from that shown. As the cantilevered probe cools down from the energy release, the piezoelectric element output signal 96c generally decreases towards a baseline with relatively small peaks coinciding with periodic heating cycles 94c applied to the cantilevered probe, as indicated in FIG. 8c. Heat pulses of the periodic heating cycles may be tailored, for example, to allow the cantilevered probe to reach characteristic melting, evaporation, and deflagration temperatures associated with a given explosive material.

Figure 9:
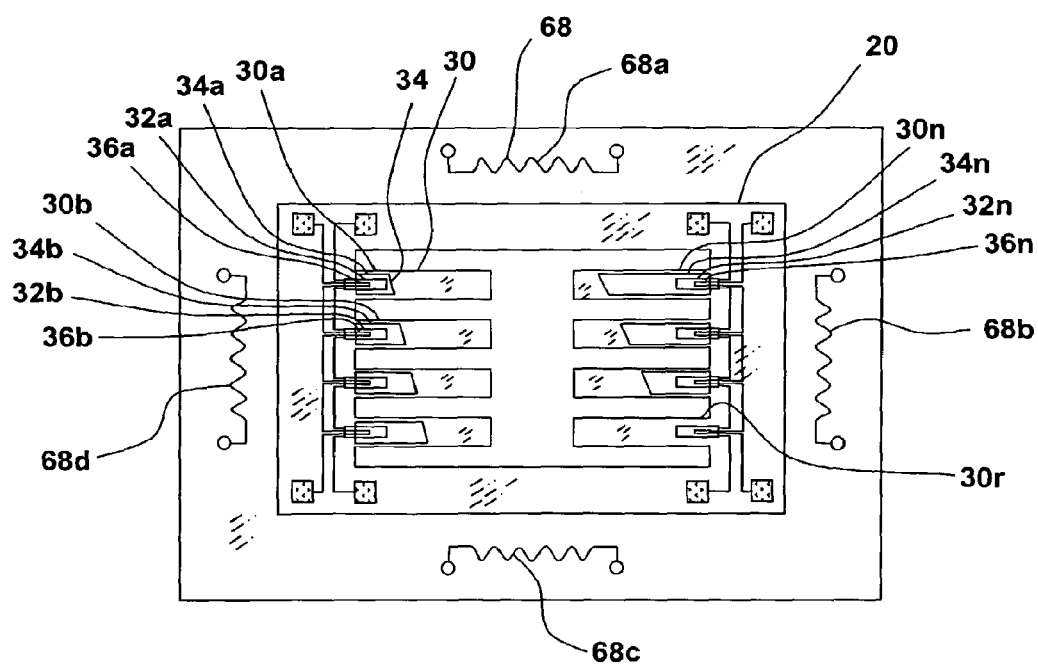
FIG. 9 is a plan view of an array of cantilevered probes with an explosive material concentrator surrounding the cantilevered probe array, in accordance with some embodiments of the current invention.

FIG. 9 illustrates an array of cantilevered probes with an explosive material concentrator surrounding the cantilevered probe array, in accordance with some embodiments of the present invention. One or more selective coatings 34 are optionally applied to the cantilevered probe array 20 having a plurality of self-sensed cantilevered probes 30. In the example shown, the cantilevered probes 30a, 30b, 30n are selectively coated with selective coatings 34a, 34b, 34n, respectively. The reference cantilevered probe 30r is shown with no coating.

In this example, the cantilevered probes 30a, 30b, 30n are nominally the same size and thickness. Frequency differentiation for this set of cantilevered probes can be achieved by varying the area of the cantilevered probes that is covered by the coating. Different amounts of selective coating material can be disposed on each cantilevered probe, varying the effective mass of each cantilevered probe and changing the resonant frequencies accordingly. Piezoelectric elements 32a, 32b, 32n and probe heaters 36a, 36b, 36n on the cantilevered probes 30a, 30b, 30n and 30r, respectively, may be coated, partially coated, or uncoated with the selective coatings 34.

An explosive material concentrator 68 can be coupled to one or more cantilevered probes 30. The concentrator 68, such as a condenser and heater system, may be included to concentrate the explosive material and/or other target chemical species 12 proximal to the cantilevered probe array 20 for detection. In some embodiments, the concentrator 68 with one or more heaters 68a, 68b, 68c and 68d surrounding the cantilevered probe array 20 is heated after the explosive material is adsorbed thereon, increasing the concentration of the explosive material in the vicinity of the cantilevered probes 30 and allowing a higher adsorption rate of the explosive material onto one or more of the cantilevered probes 30. The heaters 68a, 68b, 68c and 68d that surround the cantilevered probe array 20 can comprise, for example, discrete heaters, integrated resistive heaters, or integrated circuitry.

Figure 10:
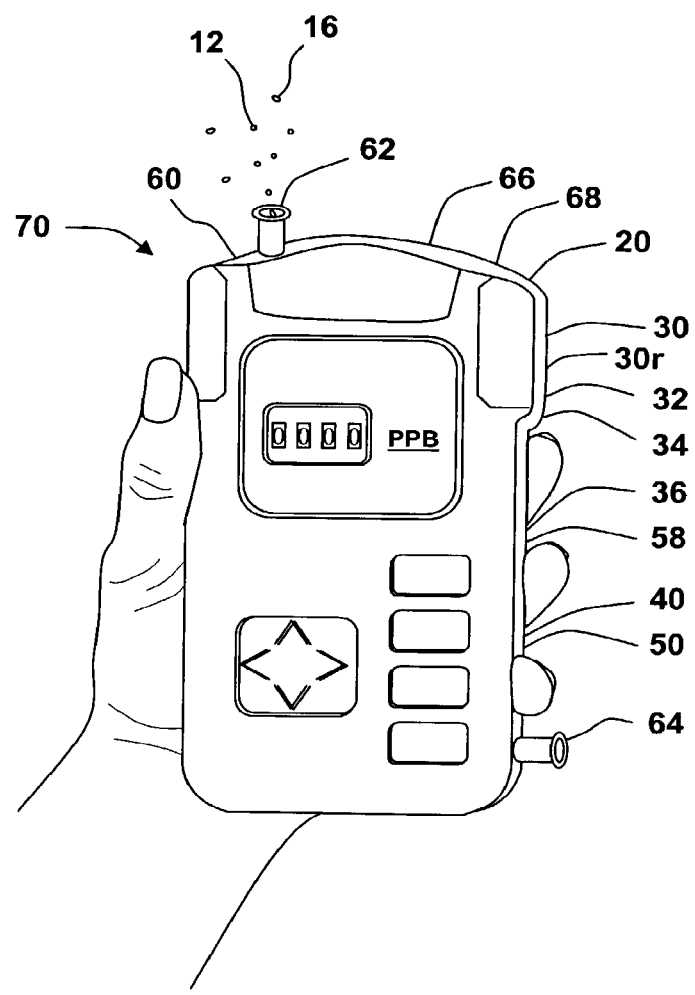
FIG. 10 is a perspective view of a handheld system for detecting an explosive material, in accordance with some embodiments of the current invention.

FIG. 10 illustrates a handheld system for detecting an explosive material, in accordance with some embodiments of the present invention. As shown, the handheld system 70 includes an enclosure 60, one or more cantilevered probes 30 within the enclosure 60, probe heaters 36 thermally coupled to the cantilevered probes 30, and piezoelectric elements 32 disposed on the cantilevered probes 30. One or more of the cantilevered probes 30 in the cantilevered probe array 20 have probe heaters 36 to locally heat selected cantilevered probes 30. Piezoelectric elements 32 can be configured to detect an explosive material 16 adsorbed onto the cantilevered probes 30 when the probe heaters 36 heat the cantilevered probes 30.

In some embodiments, the piezoelectric element 32 also serves as a piezoelectric drive and as a piezoelectric sense mechanism. The piezoelectric element 32 can detect the explosive material 16 adsorbed onto one or more of the cantilevered probes 30. One or more selective coatings 34 may be applied to one or more of the cantilevered probes 30 in the cantilevered probe array 20. An interface circuit 40 may be coupled to the cantilevered probe array 20. The enclosure 60 can have an inlet port 62 to allow ingression of the explosive material 16 into the enclosure 60 and an outlet port 64 to allow egression of the explosive material 16 or a byproduct thereof from the enclosure 60. When the cantilevered probe array 20 is exposed to the explosive material 16 and the interface circuit 40 actuates the cantilevered probe array 20 during or after heating, one or more of the cantilevered probes 30 in the cantilevered probe array 20 may exhibit a response such as a resonant frequency shift, a shift in bending, a thermal signature, a recoil response such as an impulse followed by ring down, a pyroelectric charge generation, an impedance shift, a temperature shift, or a combination thereof.

The cantilevered probe array 20 may include a plurality of cantilevered probes 30 that are frequency-differentiated. The plurality of cantilevered probes 30 in the cantilevered probe array 20 may be electrically connected to a single pair of cantilevered probe array drive pads, and one or more groups of cantilevered probes 30 may be included within the enclosure 60.

The handheld system 70 may include a controller 50 in communication with the interface circuit 40. The controller 50 can be configured to receive a shifted cantilevered probe response and piezoelectric element output signals from a set of cantilevered probes 30 in the cantilevered probe array 20. The shifted cantilevered probe responses and the piezoelectric element output signals can be analyzed and used to determine the constituency and concentration of the explosive material 16.

The cantilevered probe array 20 may include a reference cantilevered probe 30r. The reference cantilevered probe 30r may provide a reference cantilevered probe response when the cantilevered probe array 20 is exposed to the explosive material 16 and the target chemical species 12.

The handheld system 70 may include a thermally conductive mesh 58 such as a copper or metal screen substantially surrounding cantilevered probes 30, such as to limit the egression of thermal energy from an exothermic reaction when the probe heater heats the cantilevered probe. The handheld system 70 also may include a transport mechanism 66 such as a pump, fan or blower and ductwork or piping for transporting the explosive material 16 and/or the target chemical species 12 to the cantilevered probe array 20. The handheld system 70 may include a concentrator 68 such as a compressor or a condenser to concentrate the explosive material 16 proximal to one or more of the cantilevered probes 30 in the cantilevered probe array 20. In some embodiments, one or more heaters of the concentrator 68 are located near the cantilevered probe array 20 so that the explosive material 16 is concentrated on one or more of the cantilevered probes 30 when the concentrator 68 is locally heated to desorb the explosive material collected by the concentrator 68.

Command and data entry input devices such as buttons, keypads, or softkeys, can be incorporated to allow the selection of functions and operation of the handheld system 70. Results of measurements can be displayed on an output device, such as an LCD, or communicated to another analysis system through a wired communication port such as a universal serial bus (USB) port or through a wireless communication protocol.

Figure 11:
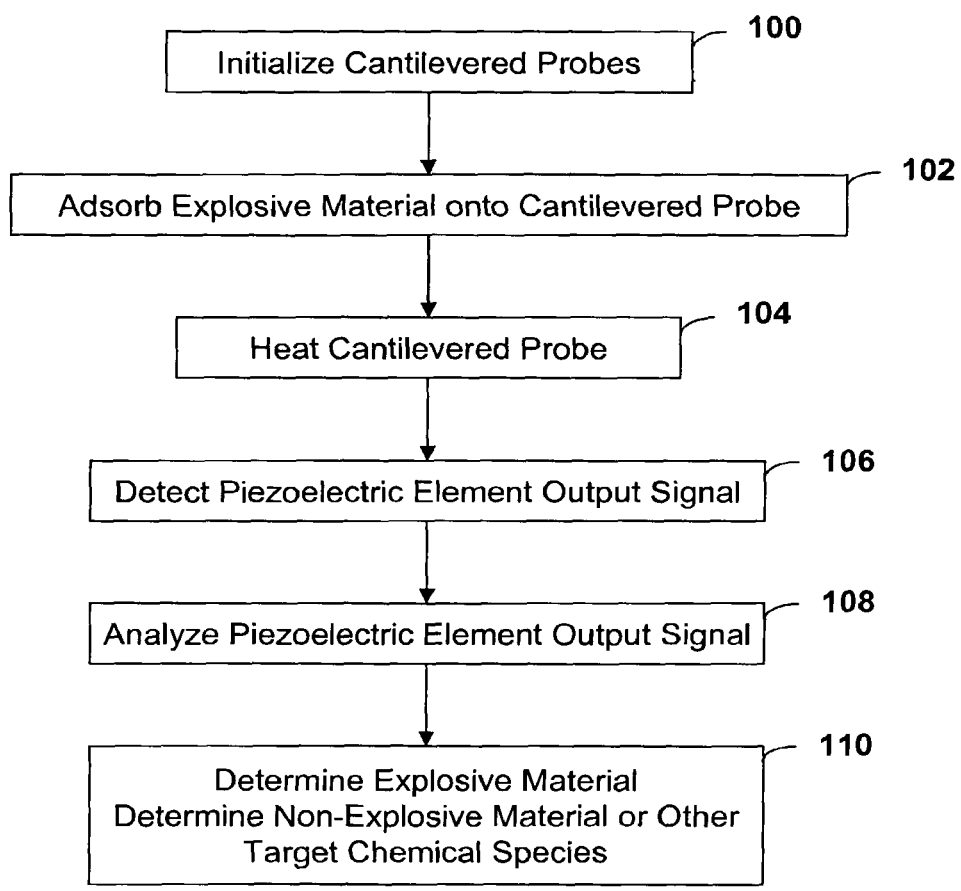
FIG. 11 is a flow chart of a method for detecting an explosive material, in accordance with some embodiments of the current invention.

FIG. 11 is a flow chart of a method for detecting an explosive material, in accordance with some embodiments of the present invention. The chemical detection method can include various steps to detect and identify one or more explosive materials and/or target chemical species, such as with a self-sensed cantilevered probe array that includes a piezoelectric element disposed on one or more cantilevered probes in the cantilevered probe array.

The cantilevered probes in the cantilevered probe array may be frequency-differentiated, separated in the frequency domain such that any one of the cantilevered probes can be measured independently of the others using, for example, a frequency generator, a frequency synthesizer, a controlled oscillator, or an impedance analyzer when the cantilevered probes are configured in series or in parallel with other cantilevered probes. The cantilevered probe array includes, for example, at least two-series connected cantilevered probes electrically connected to a pair of cantilevered probe array drive pads. Alternatively, the cantilevered probe array may include at least two parallel-connected cantilevered probes electrically connected to a pair of cantilevered probe array drive pads. Alternatively, the cantilevered probe array may include a network of series-connected and parallel-connected cantilevered probes electrically connected to a pair of cantilevered probe array drive pads. One or more groups of cantilevered probes may be connected to the same set of cantilevered probe array drive pads or to a different set of cantilevered probe array drive pads on the same substrate for external connection to an interface circuit.

The cantilevered probe array may include one or more selective coatings applied to one or more cantilevered probes in the cantilevered probe array. Exemplary chemical-sensitive coating materials include an epoxy resin, a fluoropolymer, a gold layer, a palladium layer, an alcohol-absorbent polymer, a water-absorbent material, a chemical-sensitive polymer, a chemical-sensitive layer, a biosensitive material, a thiol, and derivatives and combinations thereof. The selective coating can be applied, for example, by standard deposition techniques such as sputter depositions, electron beam depositions, or plasma-enhanced chemical vapor depositions, or by dipping, spraying or dispensing the coating material onto at least a portion of one or more cantilevered probes. In another example, a chemical-sensitive selective coating is applied to one or more cantilevered probes with a stencil mask and the selective masking of one or more cantilevered probes. A single material may be applied through the mask.

A plurality of chemical-sensitive coating materials may be applied to a set of cantilevered probes in the cantilevered probe array. For example, multiple masks may be used for multiple coatings with different coating materials on selected portions of one or more cantilevered probes. Alternatively, coating with multiple materials through a single mask may be accomplished by spraying a non-homogenous coating material onto a set of cantilevered probes in the cantilevered probe array such that cantilevered probes in the array are coated with differences in coating constituency, thickness, or fraction of coverage.

A probe heater on or near the cantilevered probe can be thermally coupled to at least one cantilevered probe, which may be heated to initialize the cantilevered probe prior to exposing it to the explosive material or to initiate an exothermal reaction. For example, the probe heater can be used to locally heat the cantilevered probe to an elevated temperature to evaporate, burn off, or otherwise remove material from the surfaces of the cantilevered probe.

The cantilevered probe array may be initialized, as seen at block 100. Initialization of the array can be accomplished, for example, by running a scan through the resonant frequencies of the cantilevered probes in the cantilevered probe array to establish a baseline or to ensure that all the cantilevered probes and the interface electronics are functioning properly.

Explosive material can be exposed to and adsorbed onto one or more cantilevered probes, as seen at block 102. For example, the self-sensed cantilevered probe array can be exposed to an explosive material. A valve and associated piping may be used to expose the cantilevered probe array to the explosive material and a carrier. The explosive material may be transported to the cantilevered probe array using, for example, fans, blowers, or pumps to force flow of the explosive material and a carrier gas or liquid onto the cantilevered probe array. Convective processes or normal diffusive processes due to concentration gradients may be used, for example, to transport the explosive material to the cantilevered probe array for detection.

An explosive material, such as 2,4,6-trinitrotoluene (TNT), 2,4,6,n-tetranitro-n-methylaniline (Tetryl), 1,3,5-trinitro-1,3,5-triazacyclohexane (RDX), 1,3,5,7-tetranitro-1,3,5,7-tetrazacyclooctane (HMX), pentaerythritol tetranitrate (PETN), glycerol trinitrate (nitroglycerin), ethylene glycol dinitrate (EGDN) or derivatives or combination thereof, can be adsorbed onto one or more cantilevered probes in the cantilevered probe array.

The explosive material may be concentrated near or on the cantilevered probe array. Concentration of the explosive material may be accomplished, for example, with a compressor and a valve system to increase the pressure in the vicinity of the cantilevered probe array. A condenser and a heater may be used, for example, to collect samples of the explosive material and then release the explosive material in proximity to the cantilevered probe array. In some embodiments, a concentrator with one or more heating elements surrounding a cantilevered probe array is heated locally after an explosive material is adsorbed thereon, increasing the concentration of explosive material in the vicinity of the cantilevered probes and allowing a higher adsorption rate of explosive material onto one or more of the cantilevered probes.

The cantilevered probe can be heated to cause, for example, an exothermic reaction or a phase change with the adsorbed explosive material, as seen at block 104. The probe heaters coupled to one or more cantilevered probes may be heated to react the explosive material. The piezoelectric element may generate a piezoelectric element output signal when the explosive material is reacted. Alternatively, the reaction of the explosive material can result in the volatile material being desorbed from a cantilevered probe, which causes a shift in the resonant frequency of the cantilevered probe due to its decreased mass. Alternatively, the reaction of the explosive material may result in a formation of a material on the surface of the cantilevered probe that increases the vibrational stiffness of the cantilevered probe and produces a frequency shift. Alternatively, reaction of the explosive material may result in a stressed film on the surface of the cantilevered probe that causes a static deflection of the cantilevered probe. The static deflection can be measured, for example, with a tapping mode where the cantilevered probe is tapped against a reference surface at a fixed distance away from the cantilevered probe, or with a tapping mode where the cantilevered probe is tapped against an adjustable mechanical stop that is adjusted so the cantilevered probe has a consistent amount of contact with the mechanical stop. Alternatively, recoil of the cantilevered probe when the adsorbed explosive material is ignited or deflagrated may produce an impulse response with a ring-down characteristic to identify the event.

A piezoelectric element output signal can be detected, as seen at block 106. The piezoelectric element output signal generated by the piezoelectric element can be detected, for example, with an analog-to-digital converter or a threshold detector. To validate the measurement, additional cantilevered probe responses may be detected. A cantilevered probe response may be detected, for example, from at least one self-sensed cantilevered probe in the cantilevered probe array by actuating one or more cantilevered probes.

In some embodiments, an exposed cantilevered probe array is actuated by applying an excitation voltage to a piezoelectric material disposed on each cantilevered probe in the cantilevered probe array. The exposed cantilevered probe array can be actuated with a signal generator or a frequency generator by scanning the cantilevered probes through a predetermined frequency range, allowing the resonant frequencies of one or more cantilevered probes to be determined. In another example, the exposed cantilevered probe array is actuated by driving the exposed array at a resonant frequency of one cantilevered probe in the cantilevered probe array, then switching as desired to a resonant frequency of another cantilevered probe for additional measurements. In another example, the exposed cantilevered probe array is actuated by driving the exposed array at a predetermined frequency, wherein the predetermined frequency is off-resonance with respect to at least one cantilevered probe in the cantilevered probe array. In another example, the amplitude of vibration is controlled as the cantilevered probe strikes against a fixed or adjustable mechanical stop. In another example, the exposed cantilevered array is actuated with an electrical impulse applied to the cantilevered probe array.

The piezoelectric element output signal can be analyzed, as seen at block 108. Analyzing the piezoelectric element output signals and the cantilevered probe response from one or more actuated cantilevered probes comprises, for example, measuring a shifted resonant frequency, a shifted Q factor, a shifted impedance, a shifted phase, a shifted deflection amplitude, or a combination thereof and comparing the responses to known or calibrated responses. A fast Fourier transform (FFT) may be performed on the cantilevered probe responses from one or more actuated cantilevered probes. The entire array of cantilevered probes, a subset thereof, or an individual cantilevered probe may be addressed by selective actuation and detection. With the availability of a reference cantilevered probe, a reference cantilevered probe response may be detected from one or more reference cantilevered probes in the cantilevered probe array. The explosive material may be determined based on comparing a measured shift from one or more actuated cantilevered probes to a reference set of cantilevered probe responses, and determining the explosive material based on the reference set of cantilevered probe responses.

The explosive material can be determined, for example, based on the piezoelectric element output signal from a piezoelectric element disposed on the cantilevered probe, as seen at block 110. Alternatively or in addition to, a non-explosive material may be adsorbed onto the surface of the cantilevered probe and determined Determining the explosive material, non-explosive material or other target chemical species may include, for example, analyzing the piezoelectric element output signal and other cantilevered probe responses such as a resonant frequency shift of the cantilevered probe, a shift in bending of the cantilevered probe, a thermal signature, a recoil response, a pyroelectric charge generation, an impedance shift, a temperature shift, or a combination thereof.

To determine the explosive material or other target chemical species, the self-sensed cantilevered probe array may be scanned through a predetermined frequency range. When activated, for example, with an interface circuit that scans through the resonant frequencies of one or more cantilevered probes, each cantilevered probe, in turn, may be excited and oscillated by the interface circuit as the frequency of the oscillator or frequency generator is scanned through each resonant frequency. Depending on the type and amount of a explosive material and the coating on the cantilevered probe, the cantilevered probes in the array may exhibit shifted cantilevered probe responses such as a shifted resonant frequency, a shifted Q factor, a shifted impedance, a shifted phase, a shifted deflection amplitude, or a combination thereof.

Temperature measurements from one or more probe heaters serving as a temperature sensor or other on-board temperature sensors may be used to indicate the temperature of the heated cantilevered probe, from which the ignition temperature of the explosive material can be determined Characteristic properties such as the heat of vaporization, melting temperature, phase change, chemical reactions, exothermic reactions, or endothermic reactions associated with adsorbed explosive material and other target chemical species may be interpreted to aid in the determination of the explosive material or target chemical species.

A controller or a software application running on a computer or digital device may be used to analyze the cantilevered probe responses and determine one or more components and their concentration in the sample. The explosive material may be determined in part based on the detected reference cantilevered probe response, for example, by a common mode correcting for effects such as temperature, pressure and viscosity of the sampled medium. The detected explosive material or target chemical species may include, for example, mercury, hydrogen, an alcohol, water vapor, a chemical element, a chemical compound, an organic material, an inorganic material, a gaseous substance, a liquid, a biological material, a DNA strand, a bioactive agent, a toxin, and derivatives and combinations thereof.

Using pattern recognition, modeling functions or signal processing techniques such as fuzzy logic, the explosive material may be determined based on comparing a measured shift from one or more actuated cantilevered probes to a reference set of cantilevered probe responses, and determining the explosive material based on the reference set of cantilevered probe responses. The reference set of cantilevered probe responses may comprise, for example, a learned set from calibration runs or from a statistical database with expectation values for various explosive materials and target chemical species.

Having illustrated and described the principles of the invention in exemplary embodiments, it should be apparent to those skilled in the art that the illustrative embodiments can be modified in arrangement and detail without departing from such principles. In view of the many possible embodiments to which the principles of the invention can be applied, it should be understood that the illustrative embodiments are intended to teach these principles and are not intended to be a limitation on the scope of the invention. We therefore claim as our invention all that comes within the scope and spirit of the following claims and their equivalents.

The invention claimed is:

1. A method for analyzing a target chemical species, the method comprising:
   driving signals to a plurality of sensor probes of a chemical detection system, the sensor probes having an outer surface including a material that interacts with one or more target chemical species;
   sensing input signals received from the sensor probes after interaction of the target chemical species with the outer surface of the sensor probes; and
   detecting, identifying, and/or characterizing the target chemical species on at least one sensor probe via a first process based on the input signals received from the sensor probe, and detecting, identifying, and/or characterizing the target chemical species on another sensor probe via a second process based on the input signals received from the sensor probe, the second process being different than the first.

2. The method of claim 1 wherein detecting, identifying, and/or characterizing the target chemical species via a first and second process occurs simultaneously.

3. The method of claim 1 further including detecting, identifying, and/or characterizing the target chemical species on another sensor probe via a third process based on the input signals received from the sensor probe, the third process being different than the first and second processes.

4. The method of claim 1 wherein the first process includes a plurality of processes.

5. The method of claim 4 wherein the plurality of processes are selected from selective adsorption of the target chemical species, selective absorption of the target chemical species, reaction of the target chemical species, phase change of the target chemical species, deflagration of the target chemical species, an impedance shift of one or more sensor probes among the plurality of sensor probes in the presence of the target chemical species, or any combination thereof.

6. The method of claim 1 wherein driving signals to a plurality of sensor probes includes driving at least one sensor probe with a waveform to induce movement in the sensor probe, and wherein sensing input signals received from the sensor probes includes sensing movements of the at least one sensor probe, and wherein one of the processes includes detecting the target chemical species through a change in movement of the at least one sensor probe as influenced by the target chemical species.

7. The method of claim 1 further comprising heating the sensor probes after interaction of the target chemical species with the outer surface of the sensor probes.

8. The method of claim 7 wherein the first or second process includes where a change in mass of the target chemical species is detectable over time as the heating evaporates the target chemical species.

9. The method of claim 7 wherein heating the sensor probes occurs while driving the sensor probes, and wherein sensing input signals includes sensing input signals received from at least one sensor probe after heating and interaction of the target chemical species with the outer surface of the sensor probe.

10. The method of claim 7 wherein driving signals to a plurality of sensor probes includes driving at least one sensor probe with a waveform and heating the at least one sensor probes to induce movement, and wherein sensing input signals received from the sensor probes includes sensing movements of the at least one sensor probe, and wherein one of the processes includes detecting, identifying, and/or characterizing the target chemical species through a change in movement of the at least one sensor probe as influenced by the target chemical species.

11. The method of claim 7 wherein driving signals to a plurality of sensor probes includes driving at least one sensor probe with a waveform and heating the at least one sensor probe to induce movement, and wherein sensing input signals received from the sensor probes includes sensing an electrical response of the at least one sensor probe, and wherein one of the processes includes detecting, identifying, and/or characterizing the target chemical species through a change in electrical impedance of the at least one sensor probe as influenced by the target chemical species.

12. The method of claim 1 wherein sensing input signals includes sensing the temperature of at least one sensor probe.

13. The method of claim 1 wherein the material of the outer surface sorbs one or more target chemical species.

14. The method of claim 1 wherein at least one sensor probe includes a unitary piezoelectric element so as to perform driving and sensing operations of the sensor probe.

15. The method of claim 1 wherein the sensor probes are connected in parallel.

16. The method of claim 1 wherein the sensor probes define an array.

17. A method for analyzing a target chemical species, the method comprising:
driving signals to a plurality of sensor probes of a chemical detection system, the sensor probes having an outer surface including a material that interacts with one or more target chemical species;
sensing input signals received from the sensor probes after interaction of the target chemical species with the outer surface of the sensor probes; and
detecting, identifying, and/or characterizing the target chemical species of each of the plurality of sensor probes via a plurality of processes based on the input signals received from the sensor probes.

18. The method of claim 17 wherein the plurality of processes are selected from selective adsorption of the target chemical species, selective absorption of the target chemical species, reaction of the target chemical species, phase change of the target chemical species, deflagration of the target chemical species, an impedance shift of one or more sensor probes among the plurality of sensor probes in the presence of the target chemical species, or any combination thereof.

19. The method of claim 17 wherein at least one sensor probe includes a unitary piezoelectric element so as to perform driving and sensing operations of the sensor probe.

20. The method of claim 17 wherein a plurality of sensor probes is connected in parallel.

21. The method of claim 17 further comprising heating a plurality of sensor probes after interaction of the target chemical species with the outer surface of the sensor probes.

22. The method of claim 17 wherein sensing input signals includes sensing the temperature of at least one sensor probe.

23. The method of claim 17 wherein the material of the outer surface sorbs one or more target chemical species.

24. A method for analyzing a target chemical species, the method comprising:
driving signals to a plurality of sensor probes of a chemical detection system, the sensor probes having an outer surface including a material that interacts with one or more target chemical species;
sensing input signals received from the sensor probes after interaction of the target chemical species with the outer surface of the sensor probes; and
detecting, identifying, and/or characterizing the target chemical species based on results from a plurality of processes and comparing those results to a database.

25. The method of claim 24 wherein the plurality of processes are selected from selective adsorption of the target chemical species, selective absorption of the target chemical species, reaction of the target chemical species, phase change of the target chemical species, deflagration of the target chemical species, an impedance shift of one or more sensor probes among the plurality of sensor probes in the presence of the target chemical species, or any combination thereof.

26. The method of claim 24 wherein at least one sensor probe includes a unitary piezoelectric element so as to perform driving and sensing operations of the sensor probe.

27. The method of claim 24 wherein a plurality of sensor probes is connected in parallel.

28. The method of claim 24 further comprising heating a plurality of sensor probes after interaction of the target chemical species with the outer surface of the sensor probes.

29. The method of claim 24 wherein sensing input signals includes sensing the temperature of at least one sensor probe.

30. The method of claim 24 wherein the material of the outer surface sorbs one or more target chemical species.

* * * * *

UNITED STATES PATENT AND TRADEMARK OFFICE
CERTIFICATE OF CORRECTION

PATENT NO. : 8,434,161 B1  
APPLICATION NO. : 13/539608  
DATED : April 30, 2013  
INVENTOR(S) : Jesse D. Adams et al.

Page 1 of 1

It is certified that error appears in the above-identified patent and that said Letters Patent is hereby corrected as shown below:

On the Title Page:

Item [63], line 1, "11/845,661" should read --12/748,788--.

Item [63], line 2, "Aug. 27, 2007" should read --Mar. 29, 2010--.

Item [63], line 2, "8,136,385" should read --8,220,067--.

In the Specification:

Column 1, line 8, "11/845,661" should read --12/748,788--.

Column 1, line 8, "8,136,385" should read --8,220,067--.

Column 1, line 9, "Aug. 27, 2007" should read --Mar. 29, 2010--.

Signed and Sealed this  
Fourteenth Day of April, 2015

Michelle K. Lee  
*Director of the United States Patent and Trademark Office*

UNITED STATES PATENT AND TRADEMARK OFFICE
CERTIFICATE OF CORRECTION

PATENT NO. : 8,434,161 B1
APPLICATION NO. : 13/539608
DATED : April 30, 2013
INVENTOR(S) : Jesse D. Adams et al.

Page 1 of 1

It is certified that error appears in the above-identified patent and that said Letters Patent is hereby corrected as shown below:

In the Specification:

Column 1, line 16, "each of which is hereby incorporated by" should read --which is hereby incorporated by--.

Signed and Sealed this
Second Day of August, 2016

Michelle K. Lee
*Director of the United States Patent and Trademark Office*